(12) United States Patent
Ingle et al.

(10) Patent No.: US 10,070,910 B2
(45) Date of Patent: Sep. 11, 2018

(54) APPARATUS AND METHODS FOR CRYOGENICALLY ABLATING TISSUE AND ADJUSTING CRYOGENIC ABLATION REGIONS

(71) Applicant: BOSTON SCIENTIFIC SCIMED, INC., Maple Grove, MN (US)

(72) Inventors: Frank W. Ingle, Palo Alto, CA (US); Robert F. Bencini, Sunnyvale, CA (US); Josef V. Koblish, Sunnyvale, CA (US); Jonathan A. Wohlgemuth, Morgan Hill, CA (US); Paul A. Roche, San Jose, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1121 days.

(21) Appl. No.: 13/938,086

(22) Filed: Jul. 9, 2013

(65) Prior Publication Data
US 2013/0289550 A1    Oct. 31, 2013

Related U.S. Application Data

(63) Continuation of application No. 12/432,538, filed on Apr. 29, 2009, now Pat. No. 8,480,663.
(Continued)

(51) Int. Cl.
*A61N 1/30*        (2006.01)
*A61B 18/02*       (2006.01)
(Continued)

(52) U.S. Cl.
CPC ......... *A61B 18/02* (2013.01); *A61M 25/1011* (2013.01); *A61B 2017/22051* (2013.01);
(Continued)

(58) Field of Classification Search
CPC ............ A61B 18/02; A61B 2018/0212; A61B 2018/0262; A61B 2018/0022; A61M 2025/1061
(Continued)

(56) References Cited

U.S. PATENT DOCUMENTS

| 4,015,606 A | 4/1977 | Mitchiner et al. |
| 5,139,496 A | 8/1992 | Hed |

(Continued)

FOREIGN PATENT DOCUMENTS

| EP | 1158906 A1 | 12/2001 |
| EP | 1303226 A2 | 4/2003 |

(Continued)

OTHER PUBLICATIONS

International Search Report and Written Opinion issued in PCT/US2009/042167, dated Aug. 7, 2009, 9 pages.
(Continued)

*Primary Examiner* — Phillip Gray
(74) *Attorney, Agent, or Firm* — Faegre Baker Daniels LLP

(57) ABSTRACT

Apparatus and methods for performing cryogenic ablation of tissue and adjusting the size and/or location of a cryogenic cooling region. A cooling assembly may include tubes for dispensing and exhausting a coolant or refrigerant. One or both of the tubes may be moved, e.g., slidably adjusted, in order to adjust the location or size of a cryogenic ablation region. The cooling assembly may be integrated into cryogenic ablation devices including a cryogenic balloon device that includes an inner inflatable balloon and another balloon that is at least partially wrapped around the inner balloon and carries refrigerant for performing cryo-ablation. Electrodes permit electrical mapping of tissue before or after cryo-ablation to verify success of the procedure.

18 Claims, 20 Drawing Sheets

Related U.S. Application Data

(60) Provisional application No. 61/053,590, filed on May 15, 2008.

(51) Int. Cl.
*A61M 25/10* (2013.01)
*A61B 17/22* (2006.01)
*A61B 18/00* (2006.01)

(52) U.S. Cl.
CPC ............... *A61B 2017/22054* (2013.01); *A61B 2018/0022* (2013.01); *A61B 2018/00196* (2013.01); *A61B 2018/0212* (2013.01); *A61B 2018/0262* (2013.01)

(58) Field of Classification Search
USPC .......................................................... 604/19
See application file for complete search history.

(56) References Cited

U.S. PATENT DOCUMENTS

| | | |
|---|---|---|
| 5,147,355 A | 9/1992 | Friedman et al. |
| 5,254,116 A | 10/1993 | Baust et al. |
| 5,334,181 A | 8/1994 | Rubinsky et al. |
| 5,674,218 A | 10/1997 | Rubinsky et al. |
| 5,759,182 A | 6/1998 | Varney et al. |
| 5,807,391 A | 9/1998 | Wijkamp |
| 6,027,499 A | 2/2000 | Johnston et al. |
| 6,106,518 A | 8/2000 | Wittenberger et al. |
| 6,231,543 B1 | 5/2001 | Hegde et al. |
| 6,235,019 B1 | 5/2001 | Lehmann et al. |
| 6,241,722 B1 * | 6/2001 | Dobak .................. A61B 18/02 606/20 |
| 6,280,439 B1 | 8/2001 | Martin et al. |
| 6,468,297 B1 * | 10/2002 | Williams ............... A61B 18/02 607/105 |
| 6,602,247 B2 | 8/2003 | Lalonde |
| 6,629,972 B2 | 10/2003 | Lehmann et al. |
| 6,682,525 B2 | 1/2004 | Lalonde et al. |
| 6,733,494 B2 | 5/2004 | Abboud et al. |
| 6,755,823 B2 | 6/2004 | Lalonde |
| 6,761,714 B2 | 7/2004 | Abboud et al. |
| 7,025,762 B2 | 4/2006 | Johnston et al. |
| 7,081,112 B2 | 7/2006 | Joye et al. |
| 7,150,745 B2 | 12/2006 | Stern et al. |
| 7,404,716 B2 | 7/2008 | Gregorio et al. |
| 2002/0045892 A1 | 4/2002 | Kramer |
| 2003/0088240 A1 * | 5/2003 | Saadat .................. A61B 18/02 606/21 |
| 2004/0243118 A1 | 12/2004 | Ayers et al. |
| 2005/0209587 A1 | 9/2005 | Joye et al. |
| 2005/0228367 A1 | 10/2005 | Abboud et al. |
| 2006/0084962 A1 | 4/2006 | Joye et al. |
| 2006/0122589 A1 | 6/2006 | Abboud et al. |
| 2006/0224153 A1 | 10/2006 | Fischell et al. |
| 2007/0161974 A1 | 7/2007 | Abboud et al. |

FOREIGN PATENT DOCUMENTS

| | | |
|---|---|---|
| EP | 1494603 B1 | 1/2005 |
| WO | 2006069013 B1 | 8/2006 |
| WO | 2008099380 A2 | 8/2008 |

OTHER PUBLICATIONS

Williams et al., "Alternative Energy Souces for Surgical Atrial Ablation," J. Card. Surgery, 2004; 19:201-206 (6 pages).

* cited by examiner

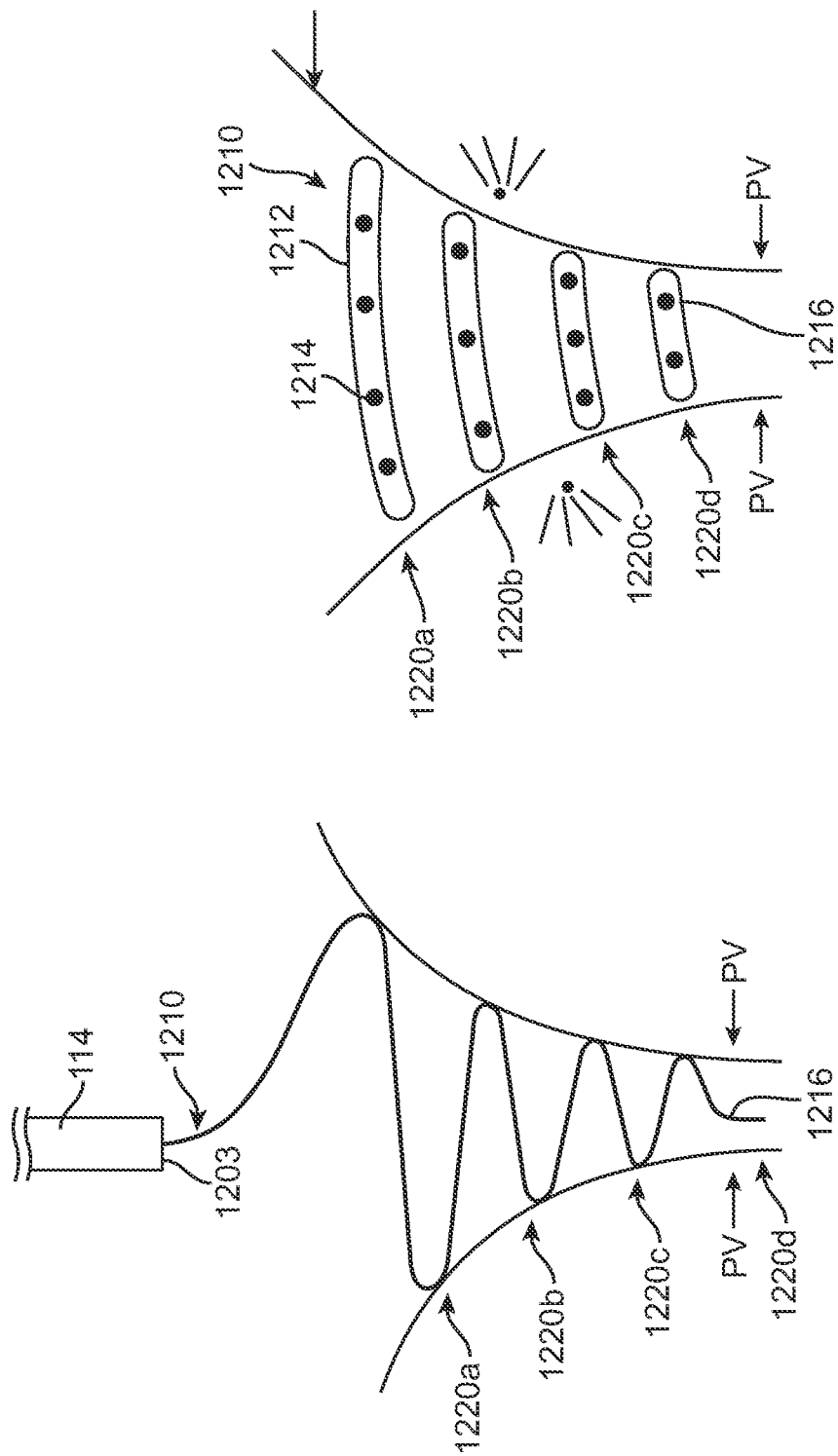

APPARATUS AND METHODS FOR CRYOGENICALLY ABLATING TISSUE AND ADJUSTING CRYOGENIC ABLATION REGIONS

RELATED APPLICATION DATA

The present application is a continuation of U.S. application Ser. No. 12/432,538, filed Apr. 29, 2009, now U.S. Pat. No. 8,480,663, which claims the benefit under 35 U.S.C. § 119 to U.S. Provisional Patent Application Ser. No. 61/053,590, filed May 15, 2008, the entirety of which are incorporated herein by reference.

FIELD OF THE INVENTION

The present inventions relate to apparatus, systems and methods for cryogenically ablating tissue such as cardiac tissue.

BACKGROUND

Cardiac arrhythmias are a significant health problem, and atrial fibrillation is a common cardiac arrhythmia that may increase risk factors for other conditions such as embolisms and contribute to the onset of ventricular arrhythmia. It is believed that atrial fibrillation is caused by certain electrical signals within the heart. It is believed that cardiac electrical impulses start in a sinoatrial (SA) node, spread through the atria, and progress through the atrial-ventricular (AV) node to the ventricles to complete a heartbeat. Atrial fibrillation is an irregular heart rhythm that is believed to originate in the atria or the upper two chambers of the heart. The pulmonary veins, in particular, can be sources of disruptive re-entrant electrical impulses that cause atrial fibrillation.

One known method of treating atrial fibrillation is by use of medication that is intended to maintain a normal sinus rate and/or decrease ventricular response rates. It is also known to use implant devices such as atrial defibrillators to treat these conditions. Other known methods and devices have been developed for creating therapeutic lesions, e.g., by minimally-invasive surgical methods, in the myocardial tissue to block unwanted electrical impulses believed to be the source of atrial fibrillation. In this context, ablation has come to mean deactivation or removal of function rather than actual tissue removal.

Formation of lesions may be performed using both endo-cardial and epicardial devices and procedures. Endocardial procedures are performed from within the heart. Since the endocardium primarily controls myocardial functions, there are inherent advantages to generating lesions by applying ablative energy to endocardial surfaces. For this purpose, it is known to use radio frequency (RF) devices or catheters and cryogenic balloon devices. Examples of known lesion formation devices, including cryogenic balloon catheters, for use in endocardial ablation and their operation are described in U.S. Patent Application Publication No. 20060084962, U.S. Pat. Nos. 6,027,499; 6,468,297; 7,025,762; 7,081,112 and 7,150,745 and Williams, et al, "Alternative Energy Sources for Surgical Atrial Ablation", J. Card. Surgery, 2004; 19:201-206, the contents of which are incorporated herein by reference as though set forth in full.

During use of a cryo-ablation balloon catheter, a coolant or refrigerant such as nitrous oxide is delivered to a cryogenic balloon, and cryogenic cooling results from a pressure drop as the cryogenic fluid is sprayed into the interior of the balloon, thereby causing the balloon to expand against the target tissue, which is cryogenically ablated as a result of the reduced temperature. The effectiveness of cryogenic balloon catheters depends on various factors including, for example, the accurate positioning of a cryogenic ablation device, sealing of entrances into the pulmonary veins, the ability to select the depth of lesions that are formed, and the ability to monitor or determine the effectiveness of ablation. Known devices, however, have a number of shortcomings and can be improved.

For example, known ablation devices may be therapeutic in that they treat or ablate tissue, but they are not suitable for performing diagnostics, e.g., determining locations of tissue to be ablated and determining the effectiveness of tissue ablation. Consequently, during an ablation procedure, an ablation device used for delivering a refrigerant and ablating tissue must be removed and replaced with a diagnostic device to assess the ablation, followed by removal of the diagnostic device and re-insertion of the ablation device to continue ablation as necessary. This switching of therapeutic and diagnostic devices is repeated as necessary until the desired ablation effect is achieved, but this procedure is not convenient and is time consuming.

Further, the entrance to a pulmonary vein is typically not a radially symmetrical cone and instead is typically a bent flattened cone, with an adjoining ridge of tissue. Consequently, two pulmonary veins may enter the atrium so close together that their mutual entrance forms an oval antrum. With certain known devices, when a balloon is inflated, the balloon may pop out or fail to seal an antrum entrance. As a result, blood may flow under the edge of the balloon to reduce cryogenic cooling and the ability to ablate adjoining tissue, thus preventing formation of complete circumferential lesions, which are desired to electrically isolate pulmonary veins from the atrium.

SUMMARY

According to one embodiment, a cryogenic ablation apparatus includes a cryogenic element and first and second tubes. The cryogenic element includes a proximal and distal end and defines a lumen extending between the proximal and distal ends. Each of the first and second tubes has a proximal end and a distal end. The distal end of the first tube is positioned within the lumen to supply refrigerant to the cryogenic element, and the distal end of the second tube is positioned within the lumen to exhaust spent refrigerant from the cryogenic element. A cryogenic ablation region is defined between the distal end of the first tube and the distal end of the second tube, and at least one of the first and second tubes being movable to adjust the cryogenic ablation region.

Another embodiment is directed to a method of adjusting a cryogenic ablation region. The method includes positioning a cryogenic element having proximal and distal ends and defining a lumen adjacent to tissue to be ablated. The method further includes positioning a first tube and a second tube within the lumen. A cryogenic ablation region is defined between a distal end of the first tube and a distal end of the second tube. The method further includes delivering a refrigerant into the lumen through the first tube to ablate tissue adjacent to the cryogenic ablation region, exhausting spent refrigerant from the lumen through the second tube and moving a tube within the lumen to adjust the cryogenic ablation region.

According to another embodiment, a cryogenic ablation apparatus includes a cryogenic balloon and first and second tubes. The cryogenic balloon has a helical body, proximal and distal ends, and defines a helical lumen. A distal end of the first tube is positioned within the helical lumen to supply refrigerant to the cryogenic balloon, and a distal end of the second tube is also positioned within the lumen to exhaust spent refrigerant from the cryogenic balloon. A cryogenic ablation region being defined between the distal end of the first tube and the distal end of the second tube, and at least one of the first and second tubes being movable to adjust the cryogenic ablation region.

A further alternative embodiment is directed to a method of adjusting a cryogenic ablation region utilizing a cryogenic balloon having a helical body. In this method, the cryogenic balloon is positioned to tissue to be cryogenically ablated. First and second tubes are positioned within the helical lumen. A cryogenic ablation region is defined between the distal end of the first tube and the distal end of the second tube. The method further includes delivering a refrigerant into the helical lumen through the first tube to ablate tissue adjacent to the cryogenic ablation region, exhausting spent refrigerant from the helical lumen through the second tube and moving a tube within the helical lumen to adjust the cryogenic ablation region.

A cryogenic ablation apparatus constructed according to another embodiment includes a support member and two balloons, e.g., two cryogenic balloons, which extend from the support member. The first balloon has a first shape, and the second balloon has a second shape that is different than the first shape. The second balloon wraps around at least a portion of the first balloon.

Another embodiment is directed to a method of cryogenically ablating tissue that includes positioning a cryogenic ablation apparatus including a support member and balloons, e.g., cryogenic balloons, which extend there from adjacent to tissue to be ablated. A first balloon has a first shape, and a second balloon has a second shape different than the first shape and wraps around at least a portion of the first balloon. The method further includes inflating the first balloon to press the second balloon against tissue to be ablated, and delivering a refrigerant into the second balloon to cryogenically ablate tissue.

According to another alternative embodiment, a cryogenic ablation system includes a support member, a cryogenic element and a cryogenic ablation region adjustment element or mechanism. The cryogenic ablation element includes first and second balloons, e.g., cryogenic balloons, which extend from the support member. The first balloon has a first shape, and a second balloon has a second shape different than the first shape. First and second tubes are positioned within a lumen defined by the second balloon, and a cryogenic ablation region is defined between a distal end of the first tube and a distal end of the second tube positioned within a lumen defined by the outer or second balloon. The first tube supplies refrigerant to the second balloon, and a distal end of the second tube is positioned within the lumen of the second balloon to exhaust spent refrigerant from the second balloon. At least one of the first and second tubes is movable within the second balloon to adjust the cryogenic ablation region.

A further embodiment is directed to a method of cryogenically ablating tissue and includes positioning a cryogenic ablation apparatus adjacent to tissue to be ablated. The ablation apparatus includes a support member, first and second balloons, e.g., cryogenic balloons, of different shapes extending from the support member such that the second balloon wraps around at least a portion of the first balloon. The method further includes inserting a first tube and a second tube into the lumen of the second balloon, a cryogenic ablation region being defined between a distal end of the first tube and a distal end of the second tube. The first balloon is inflated to press the second balloon against tissue to be ablated, and a refrigerant is delivered through the second balloon to cryogenically ablate tissue. The cryogenic ablation region is adjusted by moving at least one of the first and second tubes.

In one or more embodiments, the cryogenic element may be a catheter or a balloon element, and apparatus and methods may be applied to cryogenically ablate including cardiac tissue, e.g., when apparatus embodiments are placed within an antrum of a pulmonary vein. In one or more embodiments including multiple balloon components, a portion of a second balloon wraps around a portion of an outer surface of the first balloon, and a cryogenic ablation region may be defined around a circumference of a section of the cryogenic element. The cryogenic ablation region defined by distal ends of tubes may be defined between two non-ablation regions of the cryogenic element. In one or more embodiments, balloons may extend from a common support member or structure and/or may be attached to each other. A second or outer balloon may extend along a first portion of a first balloon and may also extend around the first balloon. The first balloon, which may be inflated, may have a bulbous, spherical or spheroid shape. At least one of the balloons, e.g., the second balloon, which may carry a refrigerant and have a helical or spiral shape, may also carry mapping electrodes or other suitable sensors for performing non-ablative, diagnostic tests, e.g., before or after cryo ablation. In one or more embodiments, the helical body defines a continuously decreasing outer diameter along its length. The helical body may have or define about one to about four loops or turns. The helical body may be composed or include a separate wire made of a memory material, such as a memory alloy, to impart a helical shape.

Further, both tubes may be moved to reposition a cryogenic ablation region and may be moved together or independently. Additionally, in one or more embodiments, a distal end of a tube, such as a first tube, that supplies refrigerant, such as nitrous oxide, is closer to a distal end of a cryogenic apparatus compared to a distal end of a tube, such as a second tube, that serves as an exhaust. In this manner, as vaporized refrigerant flows past a portion of the first tube, the vaporized refrigerate chills a distal portion of the first tube. Thus, with this configuration, refrigerant dispensed from the first tube chills a portion of the same first tube.

Embodiments may also involve mapping electrodes (or other non-ablative or non-therapeutic elements or sensors) that are carried by first and/or second balloons. In one embodiment, mapping electrodes or other diagnostic devices are carried by, e.g., mounted to, a tube that carries refrigerant.

BRIEF DESCRIPTION OF THE DRAWINGS

Referring now to the drawings in which like reference numbers represent corresponding parts throughout and in which:

FIG. 14 illustrates the spiral or helical balloon configured for insertion within an antrum of a pulmonary vein;

FIG. 15 generally illustrates a cross-sectional view of a spiral or helical balloon positioned within an antrum of a pulmonary vein and defining about four loops or turns;

DETAILED DESCRIPTION OF ILLUSTRATED EMBODIMENTS

Embodiments provide systems, apparatus and methods for use in cryogenically ablating tissue, e.g., endocardial tissue. In certain embodiments, a cryogenic ablation device includes an adjustable cooling assembly that can be used to change the shape and/or size or length of a cryogenic ablation region. In certain other embodiments, a balloon ablation device includes a helical or spiral shape, and the adjustable cooling assembly may be integrated within the helical balloon. In certain other embodiments, a cryogenic ablation device is a balloon device and may include multiple balloons, one of which is at least partially wrapped around the other balloon. In certain other embodiments, an adjustable cooling assembly is incorporated into a multi-balloon cryogenic ablation apparatus.

Figure 1:
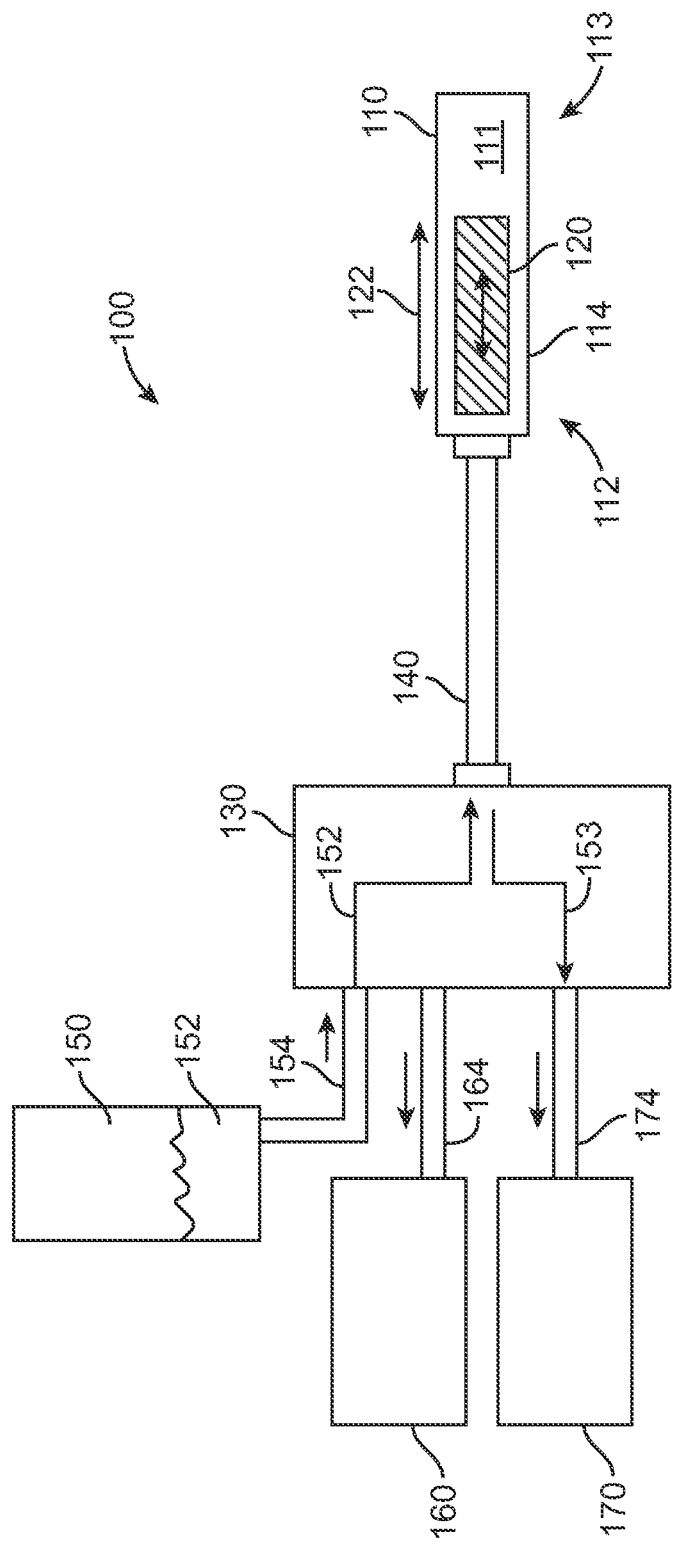
FIG. 1 schematically illustrates a cryogenic ablation system constructed in accordance with one embodiment in which a cryogenic ablation device includes a movable cooling assembly to adjust a cryogenic ablation or treatment region.
Figure 2:
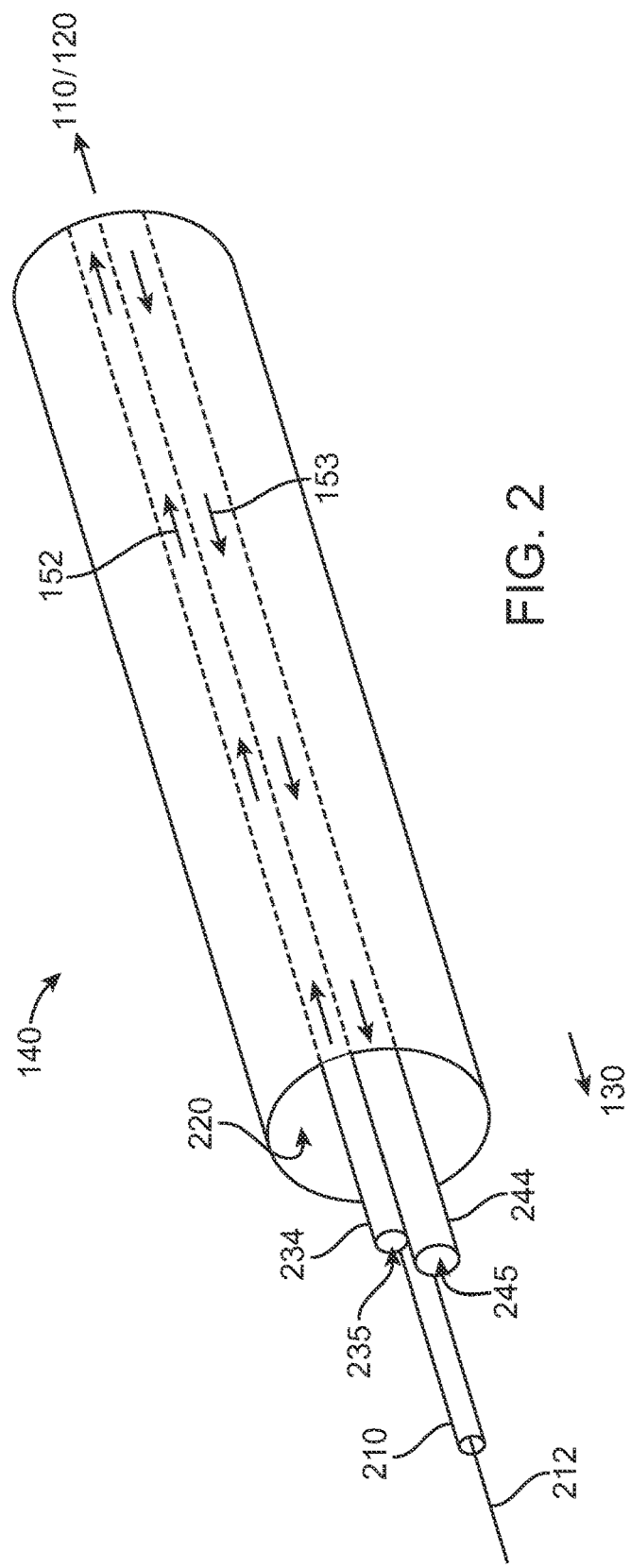
FIG. 2 illustrates an elongate flexible body or connection between a console and a cryogenic ablation device in further detail.
Figure 3:
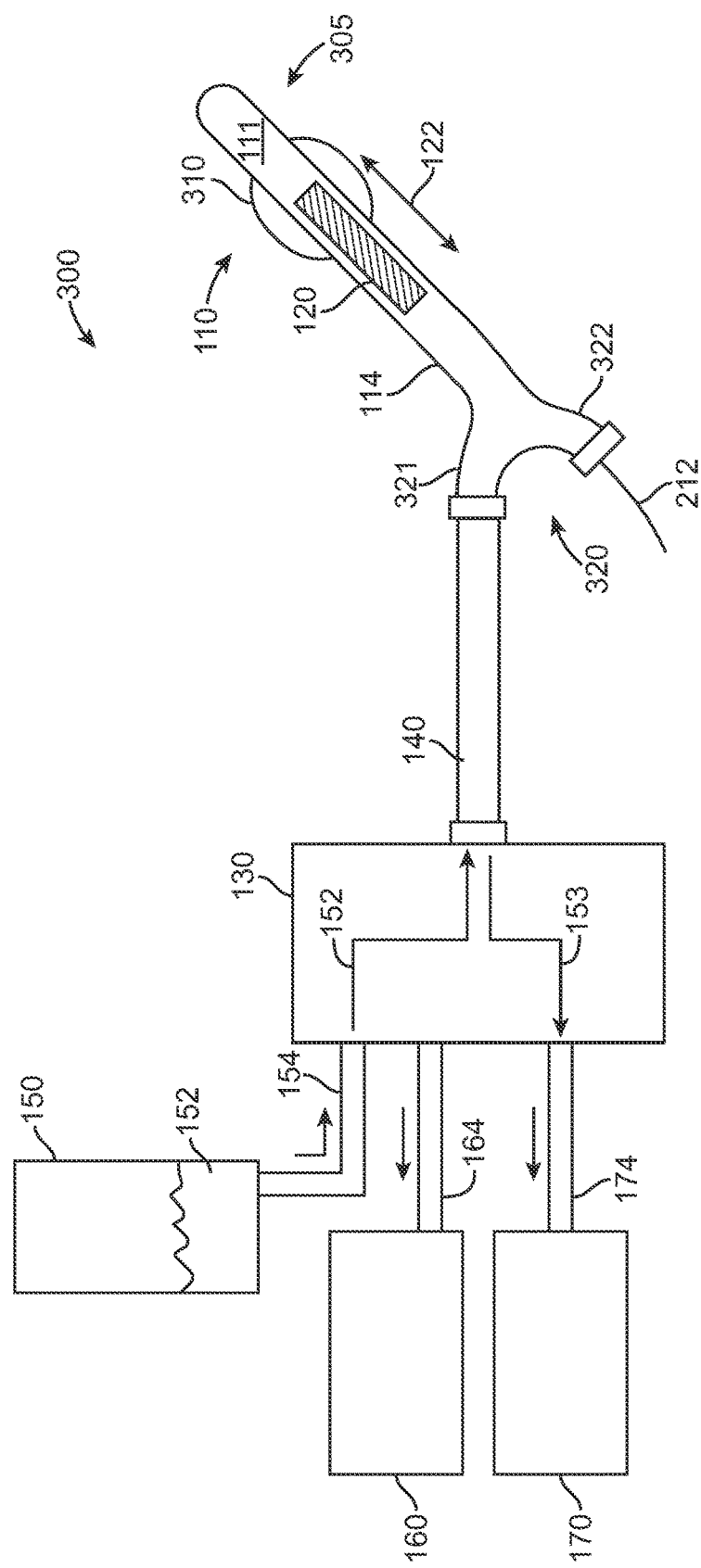
FIG. 3 schematically illustrates a cryogenic ablation system constructed in accordance with one embodiment in which a cryogenic balloon device includes a movable cooling assembly to adjust a cryogenic ablation or treatment region.
Figure 16:
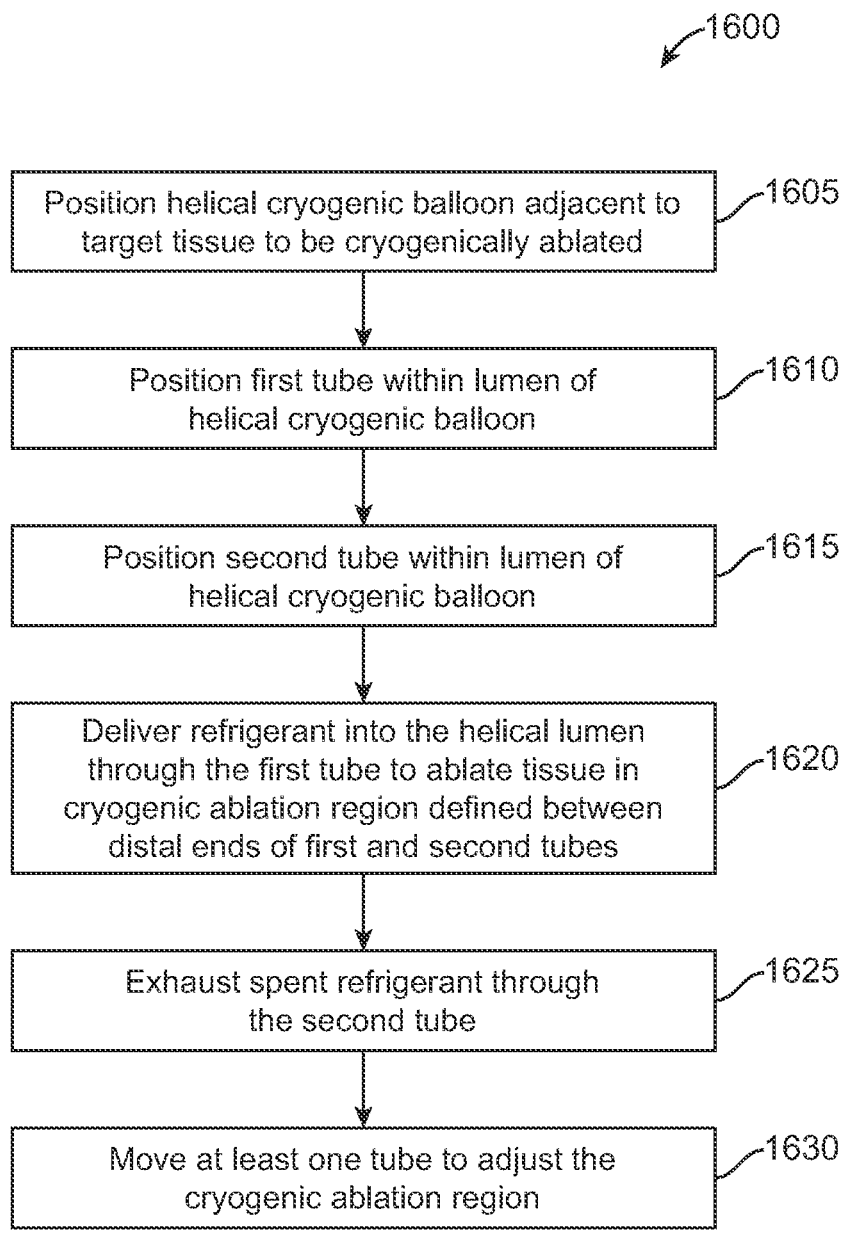
FIG. 16 is a flow chart of a method of adjusting a cryogenic ablation region of the spiral or helical balloon shown in FIGS. 13-15 utilizing a movable cooling assembly.
Figure 17:
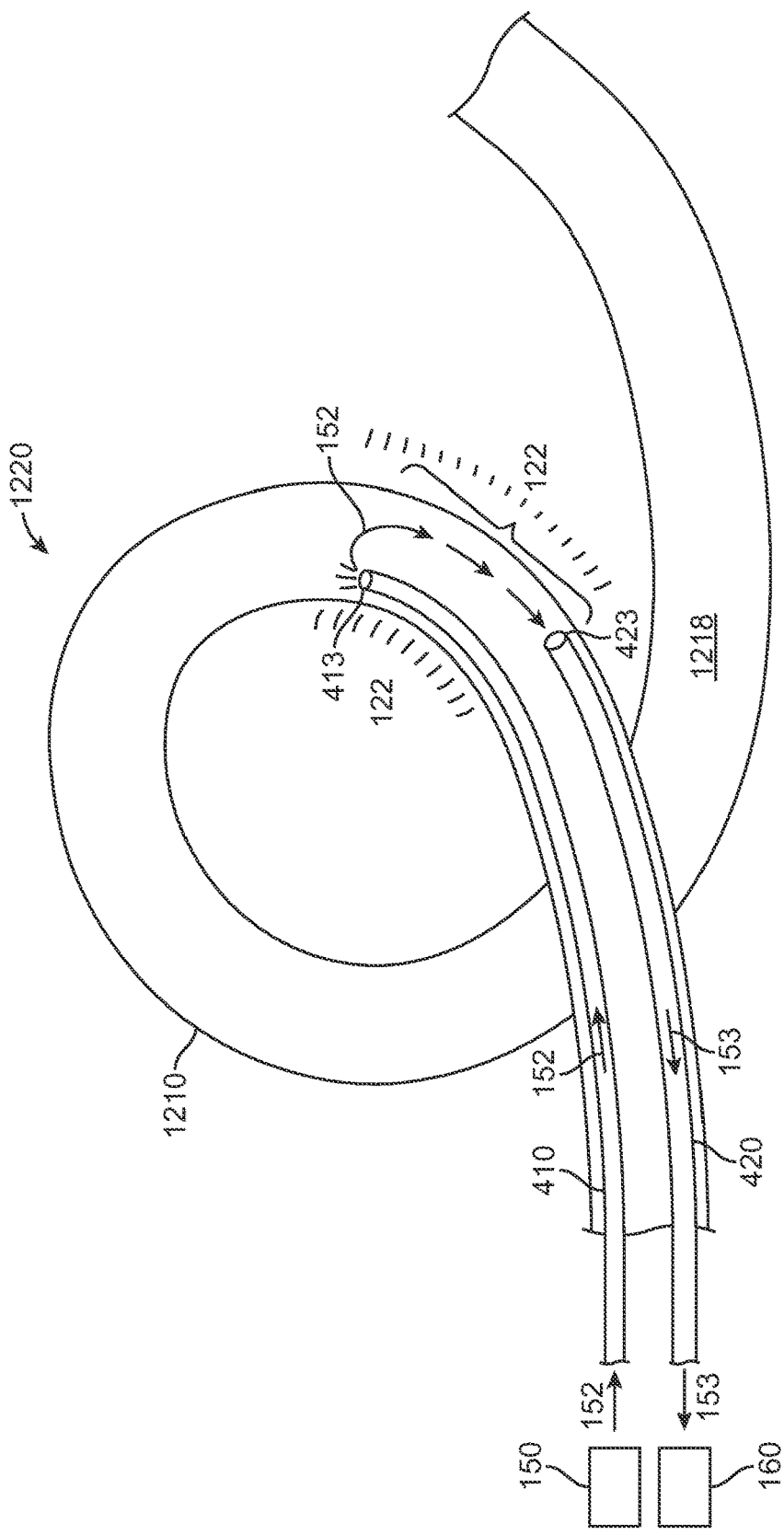
FIG. 17 further illustrates how a movable cooling assembly may be incorporated into a spiral or helical balloon shown in FIGS. 13-15 according to one embodiment.
Figure 18:
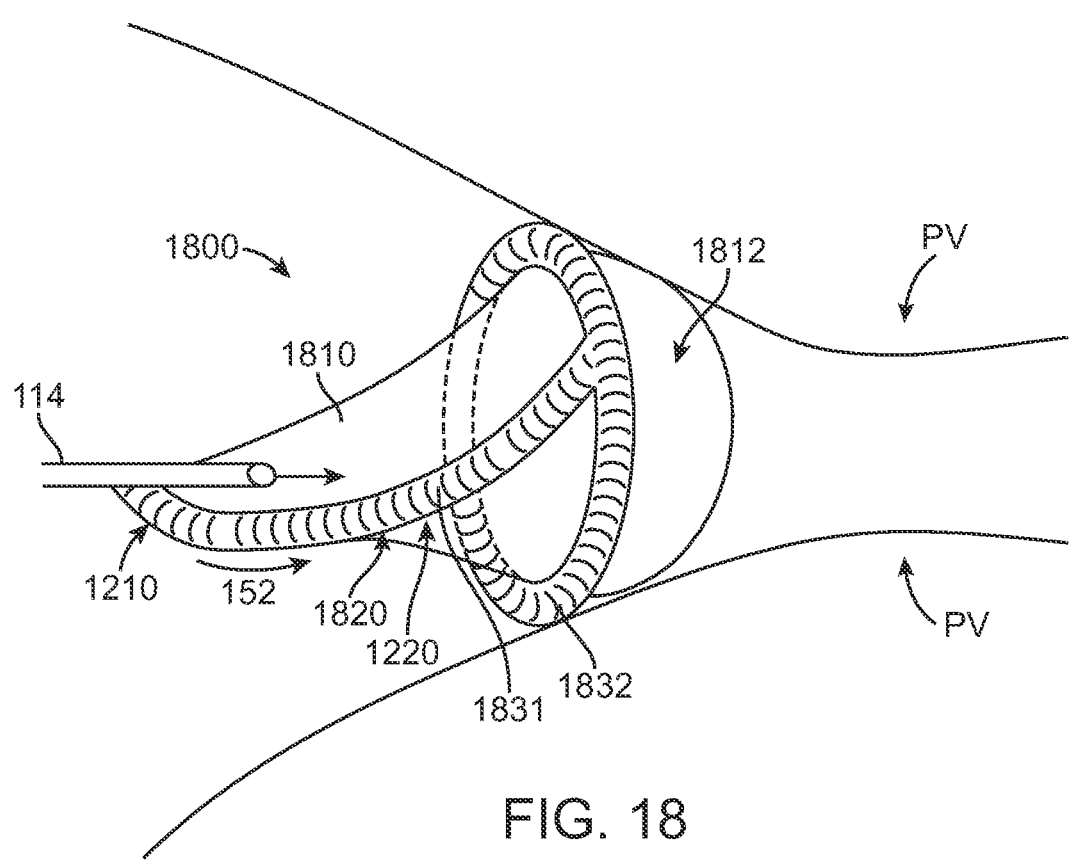
FIG. 18 illustrates a multi-balloon cryoablation apparatus constructed according to one embodiment that includes at least one balloon at least partially wound around another balloon.
Figure 19:
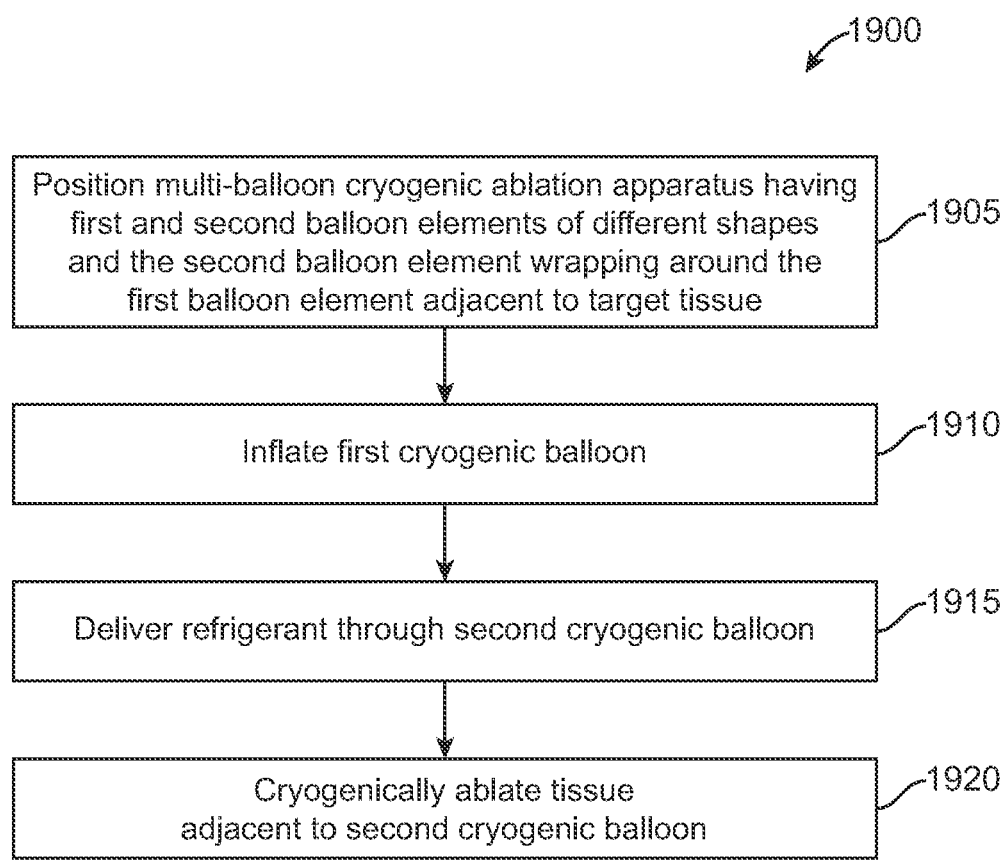
FIG. 19 is a flow chart of a method of cryogenically ablating tissue utilizing the multi-balloon apparatus shown in FIG. 18.
Figure 20:
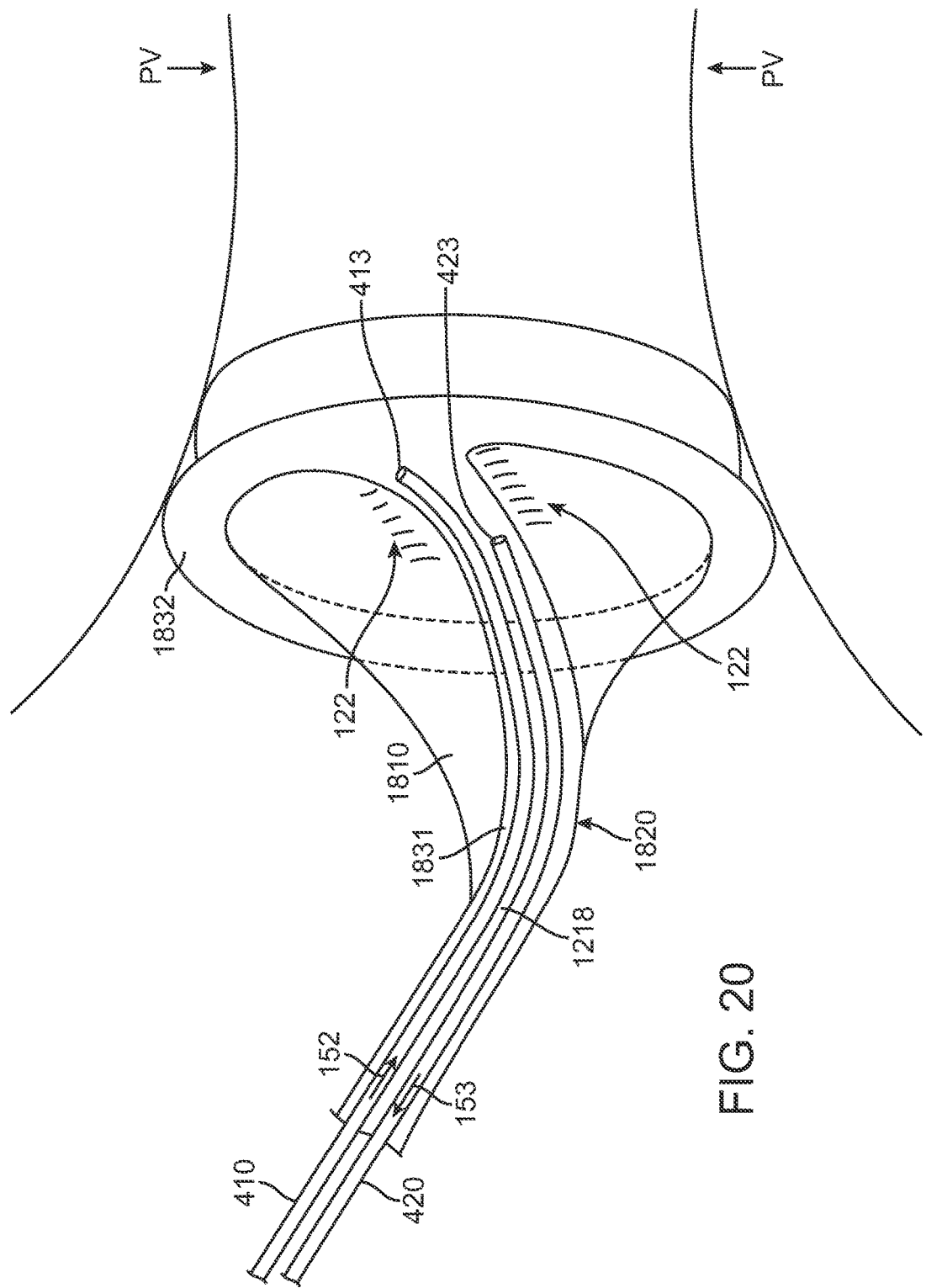
FIG. 20 illustrates how a movable cooling assembly may be incorporated into the multi-balloon cryoablation apparatus shown in FIG. 18.
Figure 21:
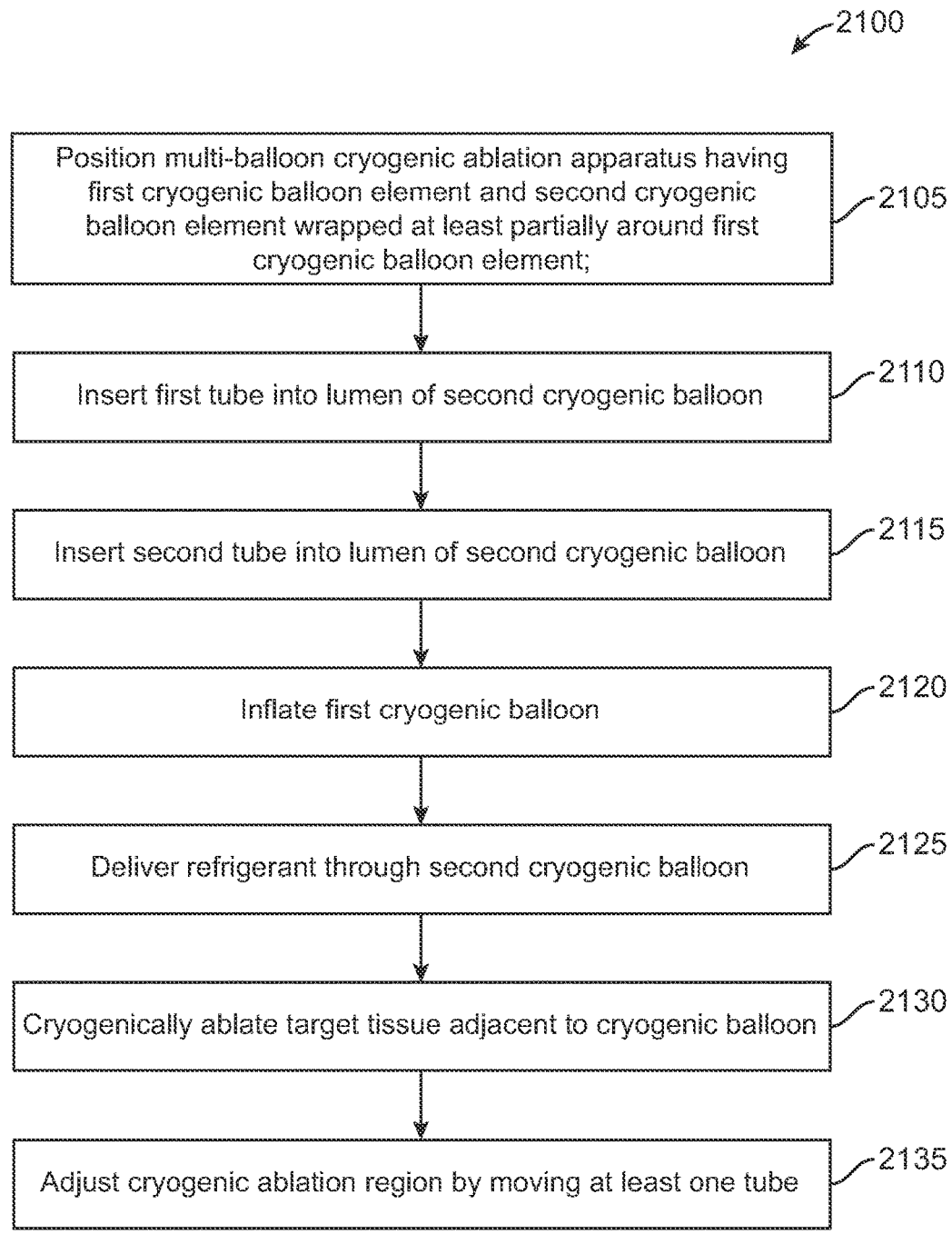
FIG. 21 is a flow chart of a method of adjusting a cryogenic ablation region of a multi-balloon apparatus utilizing a multi-balloon apparatus.

Further aspects of various embodiments are described with reference to FIGS. 1-21. FIGS. 1-3 illustrate cryogenic ablation systems constructed according to embodiments; FIGS. 4-11 illustrate aspects of embodiments of a movable cooling assembly and method of adjusting a cryogenic ablation region; FIGS. 12-15 illustrate embodiments of a cryogenic balloon element having a spiral or helical shape; FIGS. 16-17 illustrates how adjustable cooling assemblies can be incorporated into spiral or helical shaped balloons; FIGS. 18-19 illustrate embodiments of a multi-balloon cryogenic ablation device; and FIGS. 20-21 illustrate how an adjustable cooling element can be incorporated into a multi-balloon cryogenic balloon device.

Referring to FIGS. 1-2, a cryogenic ablation system 100 constructed according to one embodiment includes a cryogenic ablation device 110 that includes a body, such as an elongate, flexible body 114 that defines a lumen or inner space 111. An adjustable or movable cooling assembly 120 is disposed or positioned at least partially within the lumen or inner space 111. The cryogenic ablation device 110 is coupled to a console or other suitable interface 130 (generally referred to as console 130) through a flexible body, conduit, hose, connector 140 (generally referred to as connector 140).

The cryogenic ablation system 100 may include other components as necessary depending on the particular system configuration and ablation device 110 utilized. For example, the system 100 may include a tank or reservoir 150 of coolant or refrigerant 152 (generally referred to as coolant 152) that is in fluid communication with the console 130 via a coolant line, conduit or tube 154, a vacuum source or pump 160 that is in fluid communication with the console 130 via a vacuum line, conduit or tube 164 to control the vacuum level of the ablation device 110, and an exhaust port, tube, lumen or line 170 through which used or spent coolant 153 from the ablation device 110 is exhausted through an exhaust line 174.

As shown in FIG. 2, the connector 140 or other suitable connection component may include a tube or conduit 210 for receiving a guide wire 212 (shown in FIG. 2, but not shown in FIG. 1) that is used to manipulate and position the ablation device 110 at a desired location within a patient's body. The connector 140 may also include a portion of the coolant tube 154, or a separate coolant tube 234 that defines a lumen 235 through which coolant 152 flows, and which extends through the lumen 220 of the connector 140 such that coolant 152 is delivered to the ablation device 110. A portion of the ablation device 110, e.g., a distal or operative end or tip 113 of the ablation device 110, may be cooled sufficiently by the coolant 152 to cryogenically ablate tissue at the cryogenic ablation region 122 defined by the cooling assembly 120. The cooling assembly 120 is configured such that the location and/or size of a cryogenic ablation region 122 can be adjusted, thereby adjusting the corresponding tissue area that is ablated. An exhaust tube 174, or a separate exhaust tube 244, extends through the lumen 220 of the connector 140 between the interface 130 and the ablation device 110. Used or spent coolant 153 is exhausted from the ablation device 110 and flows through a lumen 245 of the exhaust tube 244.

According to one embodiment, as generally illustrated in FIG. 1, the ablation device 110 may be a cryogenic catheter. Referring to FIG. 3, according to another embodiment, a cryogenic ablation system 300 includes an ablation device 110 that is a cryogenic balloon catheter 305 that includes an inflatable or dilation-type balloon element 310, which may expand as coolant 152 evaporates within the cryogenic balloon catheter 305. The vacuum level within the cryogenic balloon catheter 305 may be controlled using the vacuum source 160. In the illustrated embodiment, a Y-adapter 320 is provided to connect the ablation device 110 to the connector 140. In the illustrated embodiment, the Y-adapter includes a first hub 321 for coupling a distal end the connector 140 (and the coolant and exhaust tubes 234, 244) to the ablation device, and a second hub 322 that accommodates the guide wire 212, which may include a steerable or deflectable tip for facilitating insertion and positioning of the cryogenic balloon catheter 300 within a patient. Aspects of known cryogenic ablation devices are described in U.S. Patent Application Publication No. 20060084962, U.S. Pat. Nos. 6,468,297 and 7,081,112, the contents of which are incorporated herein by reference.

According to one embodiment, the coolant 152 utilized with the ablation device 110 such as a cryogenic balloon catheter 305 is a flowable coolant, e.g., nitrous oxide ($N_2O$). Embodiments may be configured for and particularly suitable for cryogenically ablating endocardial tissue to treat atrial fibrillation and controlling or adjusting the location and/or size of the ablation region 122 utilizing nitrous oxide. It should be understood, however, that embodiments may be implemented using other coolants 152, and embodiments may be used in various other applications to cryogenically ablate different types of tissue in connection treating other conditions and diseases. For ease of explanation, reference is made to nitrous oxide as the coolant 152.

Figure 4:
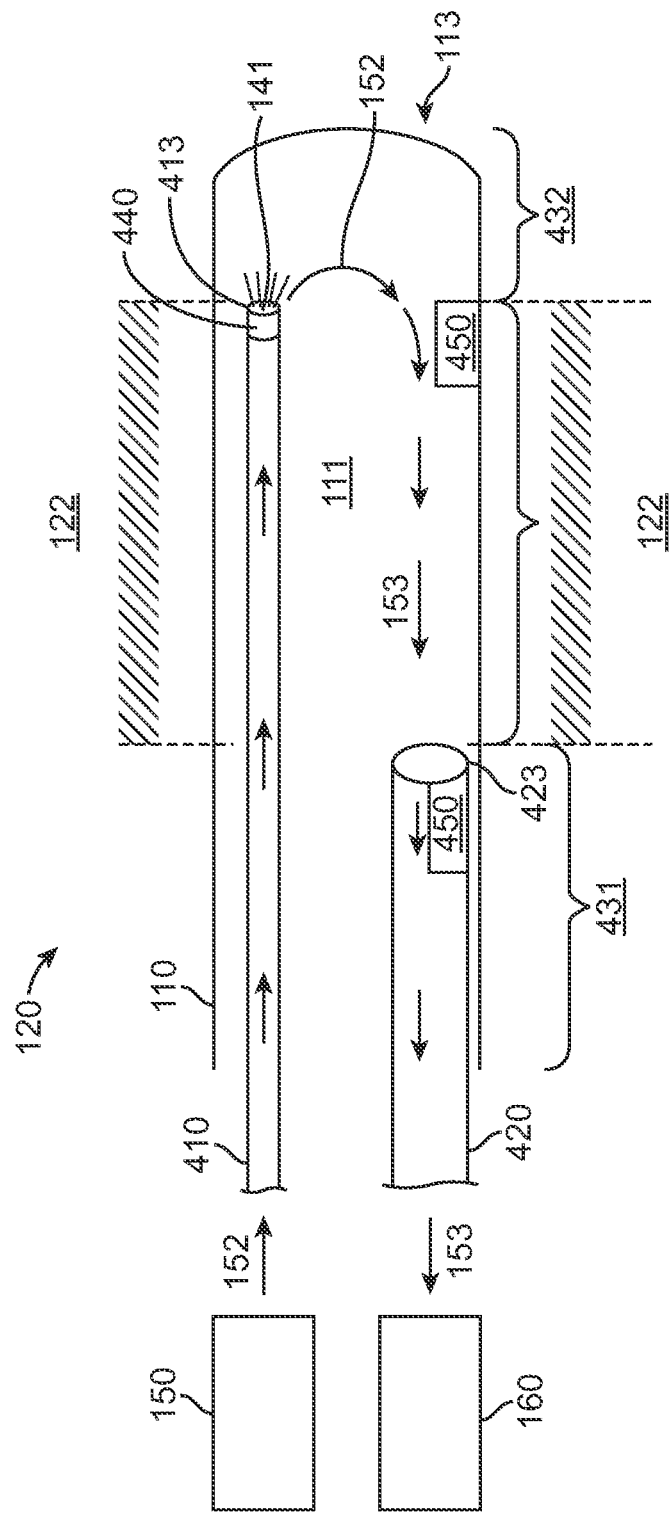
FIG. 4 illustrates a movable cooling assembly constructed according to one embodiment.

Referring to FIG. 4, a movable cooling assembly 120 constructed according to one embodiment includes multiple inner tubes. In the illustrated embodiment, the assembly 120 includes a first inner tube 410 and a second inner tube 420. The first and second inner tubes 410, 420 may be coaxial or parallel to each other (as illustrated in FIG. 4), and both of which may be positioned at least partially within the lumen or internal space 111 of the ablation device 110. The first and second tubes 410, 420 may be continuations of the supply and exhaust tubes 234, 244 shown in FIG. 2 or separate tubes as shown in FIG. 4 depending on the configuration employed. For ease of explanation, reference is made to the movable cooling assembly 120 including a first inner tube 410 for supplying coolant 152 and a second inner tube 420 for exhausting spent refrigerant 153.

As shown in FIG. 4, a temperature sensor 450 may also be positioned within the distal end 113 to provide temperature feedback and control of refrigerant 152 temperatures. According to one embodiment, the temperature sensor 450 is located within an ablation region 122 (as generally illustrated in FIG. 4). According to another embodiment, the temperature sensor 450 is located within the distal end of the second tube 420.

According to one embodiment, the first and second inner tube 410, 420 are different sizes. The small size of the nozzle 440 at the distal end of the first inner tube 410 facilitates dispersion of refrigerant 152 to maximize heat absorption after the refrigerant 152 passes through the nozzle 440. For example, the first inner tube 410 can have an inner diameter of about 0.004" such that most of the pressure loss occurs within the nozzle 440. This allows refrigerant 152 to remain as a liquid until it expands through the nozzle 440. As a further example, the second inner tube 420 has a larger inner diameter, e.g., about 0.05", such that low pressures can be maintained in the cooling region as gas is exhausted to facilitate evacuation of refrigerant 153.

Figure 5:
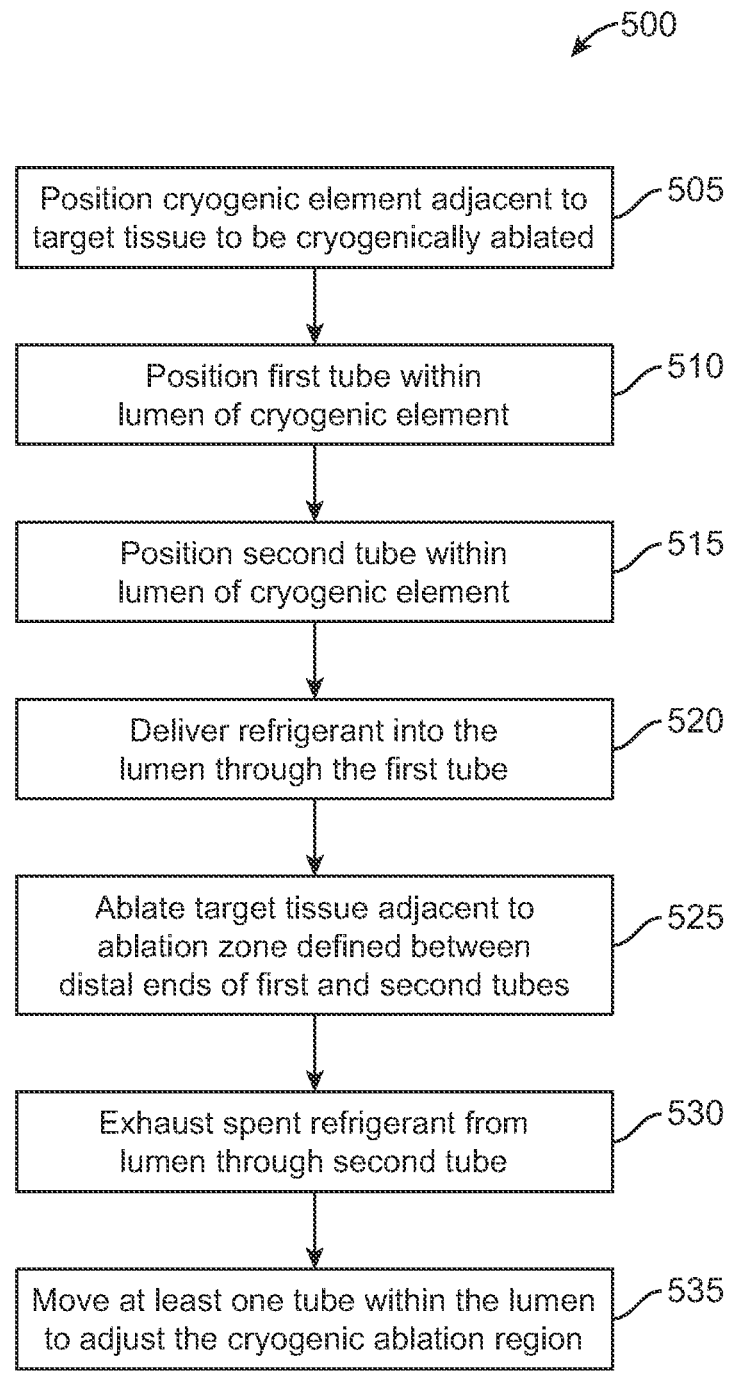
FIG. 5 is a flow chart of a method of cryogenically ablating tissue and adjusting cryogenic ablation regions according to one embodiment.

During use, with further reference to FIG. 5, a method 500 for cryogenically ablating tissue using the ablation device 110 including the movable cooling assembly 120 includes positioning the cryogenic ablation device 110 adjacent to target tissue to be cryogenically ablated at stage 505. A stage 510, if necessary, the first tube 410 is positioned within the lumen 111 of the ablation device 110. The first tube 410 carries coolant 152. At stage 515, if necessary, the second tube 420 is positioned within the lumen 111 of the ablation device 410. The second tube 420 exhausts used or spent coolant 153. In this manner, as shown in FIG. 4, a cryogenic ablation region 122 is defined between the distal end 413 of the first or coolant tube 410 and a distal end 423 of the second or exhaust tube 420. At stage 520, coolant 152 is dispersed from the first nozzle 440 of the first tube 410 and into the lumen 111 where it is vaporized and sprayed onto an inner wall of the ablation device 110.

Figure 6A:
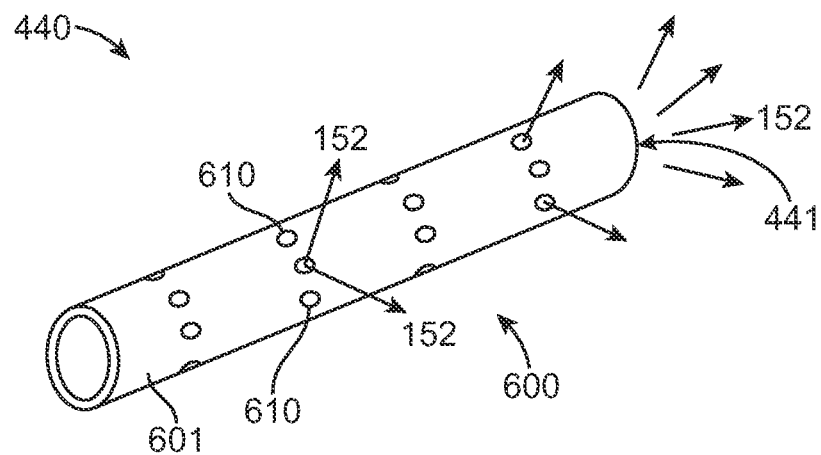
FIG. 6A schematically illustrates a nozzle including ports defined through a side wall for use in embodiments.
Figure 6B:
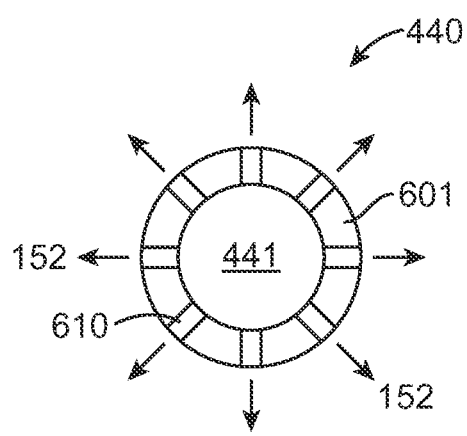
FIG. 6B is a cross-sectional view of a portion of the nozzle shown in FIG. 5A.

For example, in one embodiment, the nozzle 440 may be a single orifice 441 through which coolant 152 is dispersed (as generally illustrated in FIG. 4). In an alternative embodiment, as shown in FIGS. 6A-B, the nozzle 440 may be a tube 600 including a plurality of dispersion apertures 610 that are defined through a side or wall 601 of the tube 600. The tube 600 may also include a distal orifice 441 through which coolant 152 may be dispersed. Dispersion apertures 610 that are defined through the side wall 601 may be used to equalize cooling along the cryogenic ablation region 122, and selected dispersion apertures 610 may be staggered and/or different sizes depending on their location to achieve desired cooling and equalization effects.

Referring again to FIG. 5, at stage 525, coolant 152 generally follows the path shown by the arrows in FIG. 4, ablating surrounding or adjacent tissue within the cryogenic ablation region 122. At stage 530, spent coolant 153 is exhausted or evacuated from the lumen 111 of the ablation device 110 through the second tube 420. The coolant flow pattern shown in FIG. 4 also provides counter current heat transfer, i.e., coolant 152 flowing from the distal end 413 of the first tube 410 towards the distal end 423 of the second tube 420 may cool the distal end 413 of the first tube 410, thereby maintaining coolant 152 (e.g., in liquid or gas/liquid form) within the first tube 410 at lower temperatures so that it will not prematurely vaporize within the first tube 410 before it is dispensed through the nozzle 440.

As shown in FIG. 4, according to one embodiment, the cryogenic ablation region 422 is defined between two non-ablation regions 431, 432 due to the dispersion pattern of coolant 152 and vacuum that is applied to exhaust spent coolant 153. It should be understood, however, that during use, a certain amount of vaporized coolant 152 may be dispersed into a non-ablation region, such as region 432. This may occur, for example, if the vacuum or exhaust level is not sufficiently high to immediately draw coolant 152 into the second tube 420. However, since the proximal end and the distal end 113 are sealed or closed, it is expected that significant quantities of refrigerant gas will not flow towards the distal end 113 and into a non-ablation region 432. Thus, for ease of explanation, reference is made to coolant 152 that generally follows the flow pattern shown by arrows in FIG. 4 such that the coolant 152 flows within a cryogenic ablation region 122 that is generally defined between the distal ends 413, 423 of respective first and second inner tubes 410, 420, and spent coolant 153 is exhausted through the second tube 420. It should be understood, however, that ablation regions 122 may not be strictly defined and may not transition exactly or as sharply as shown in the FIG. 4 and other Figures, which are provided to generally illustrate how refrigerant 152 generally flows and how ablation regions 122 may generally be defined between distal ends of different tubes 410, 420.

One or both of the first and second tubes 410, 420 may be adjusted, e.g., slidably moved together or independently within the lumen 111, to adjust the location and/or size of the cryogenic ablation region 122, thereby adjusting which tissue is ablated and the ablation effect resulting from ablation regions 122 of different lengths. The manner in which the first and second inner tubes 410, 420 may be adjusted is shown in further detail in FIGS. 7-11, which illustrate cooling assembly 120 configurations relative to an initial configuration shown in FIG. 4 for reference.

Figure 7:
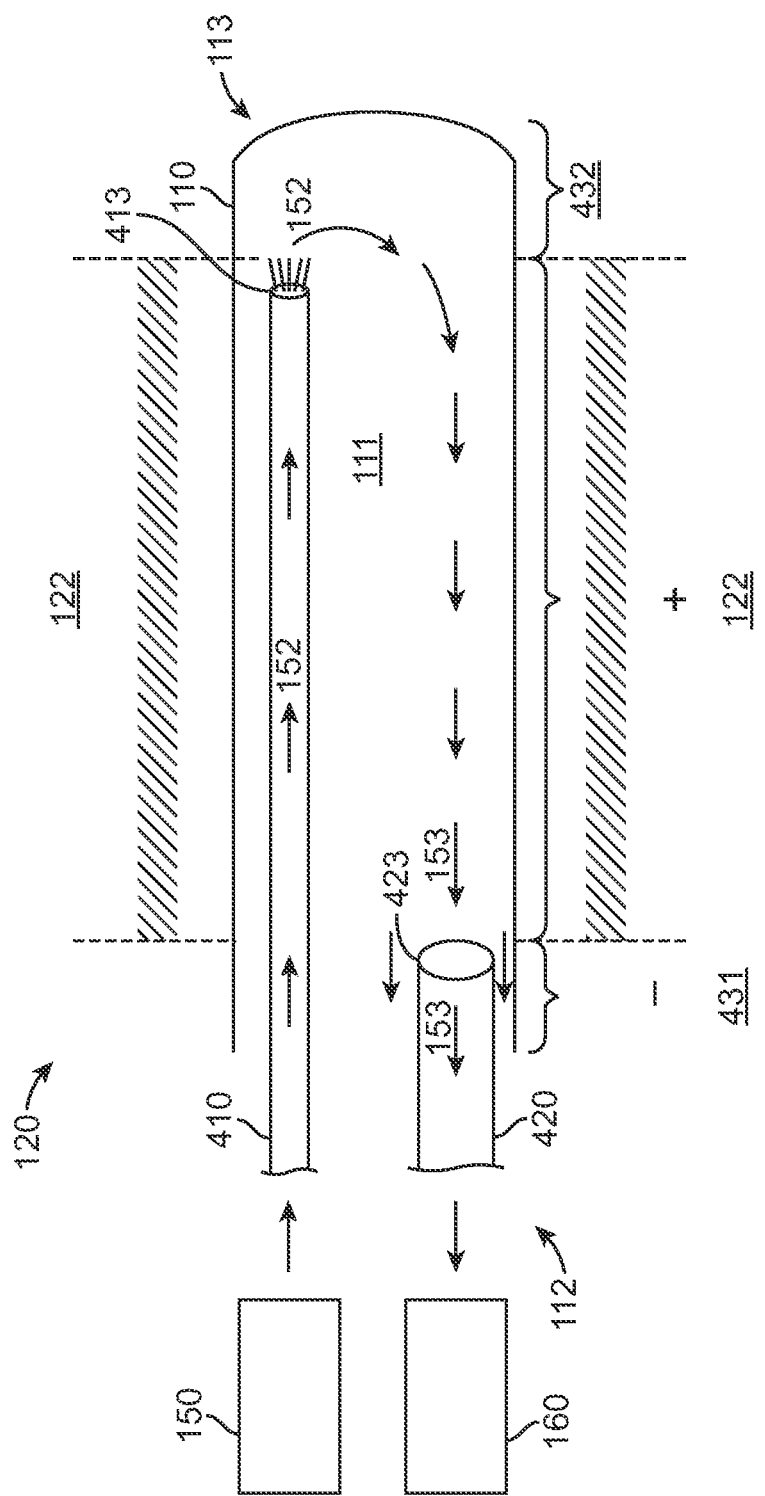
FIG. 7 illustrates the movable cooling assembly shown in FIG. 4 in which an exhaust tube is moved towards a proximal end of the ablation device to enlarge a cryogenic ablation region.

Referring to FIG. 7, according to one embodiment, one tube of the cooling assembly 120 is moved to adjust a size of the cryogenic ablation region 122. In the illustrated embodiment, the exhaust or second inner tube 420 may be pulled back such that the distal end 423 is moved towards the proximal end 112 of the ablation device 110, while the position of the first inner tube 410 remains in the same position. In this manner, the cryogenic ablation region 122 is enlarged (represented by "+") towards the proximal end 112 of the ablation device 110, the non-ablation region 431 at the proximal end 112 of the ablation device 110 is reduced in size (represented by "−"), and the size of the other non-ablation region 432 remains the same. In cases in which the cryogenic ablation region 122 is enlarged, it may be necessary to provide additional coolant 152 to ensure effective ablation of tissue surrounding or adjacent to a larger ablation region 122.

Figure 8:
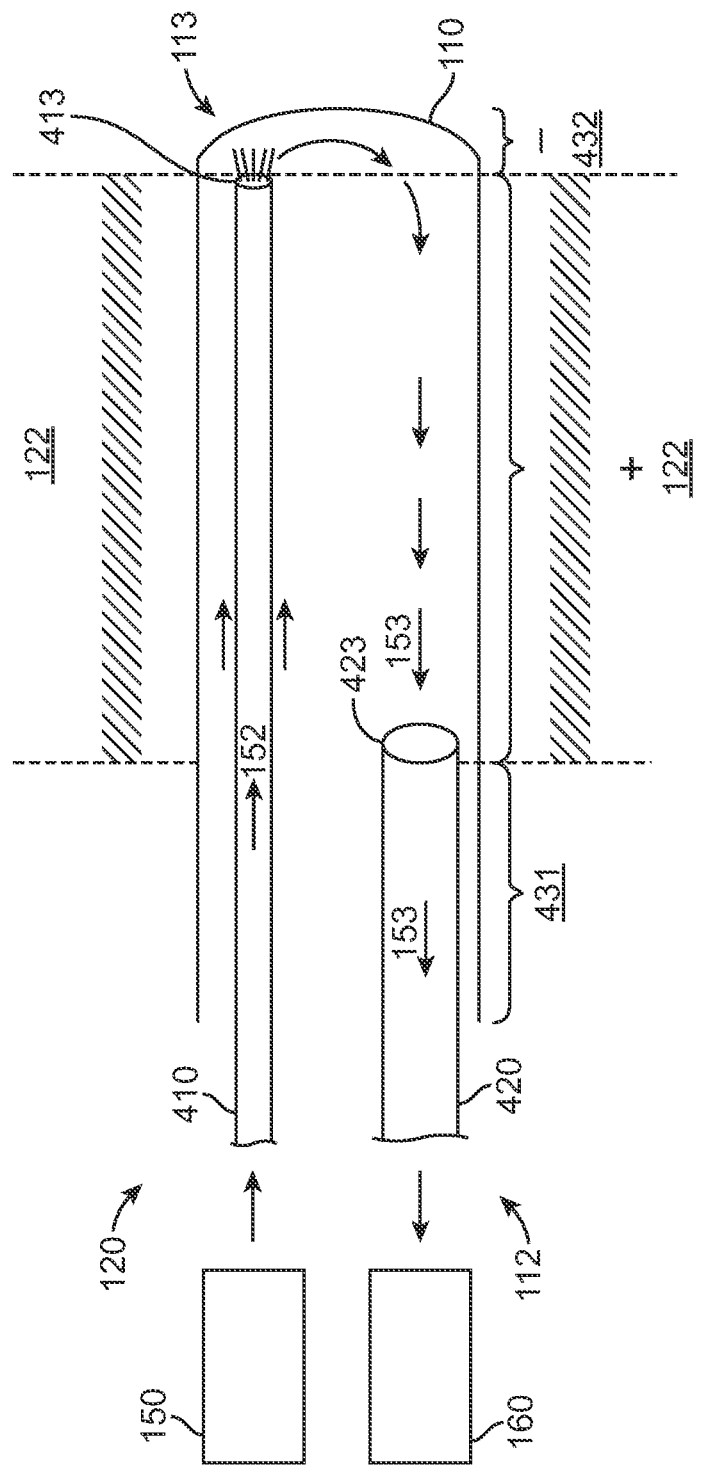
FIG. 8 illustrates the movable cooling assembly shown in FIG. 4 in which a coolant supply tube is moved towards a distal end of the ablation device to enlarge a cryogenic ablation region.

Referring to FIG. 8, according to another embodiment, the second tube 420 that carries coolant 152 is moved or pushed forward towards the distal end 113 of the ablation device 110 while the first inner tube 410 remains in the same position, thereby enlarging the cryogenic ablation region 122 (represented by "+") towards the distal end 113 of the ablation device 110 while the non-ablation region 431 remains the same size, and the other non-ablation region 432 is reduced (represented by "−").

While FIGS. 7 and 8 illustrate embodiments in which one tube is moved to expand the cryogenic ablation region 122, in another embodiment, the second tube 410 is pulled back towards the proximal end 112 of the ablation device 110 and the first tube 110 is pushed towards the distal end 113 of the ablation device 110 to expand both ends of the cryogenic ablation region 122.

Figure 9:
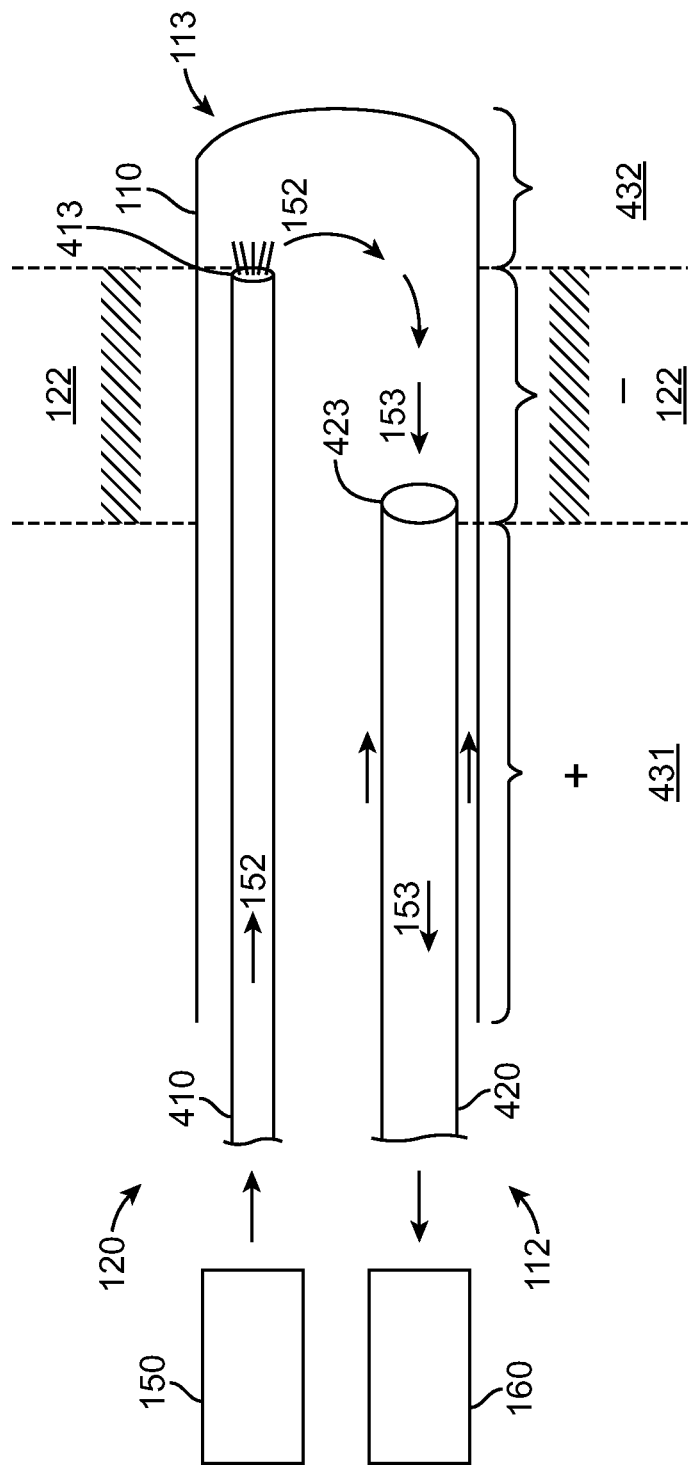
FIG. 9 illustrates the movable cooling assembly shown in FIG. 4 in which an exhaust tube is moved towards a distal end of the ablation device to reduce a cryogenic ablation region.

Similar adjustments may be made to reduce or contract or provide a more focused cryogenic ablation region 122, which may require less coolant 152 to achieve similar ablation effects. Referring to FIG. 9, according to one embodiment, the exhaust or second inner tube 420 is moved or pushed towards the distal end 113 of the ablation device 110 while the position of the first inner tube 410 remains in the same position, thereby resulting in a cryogenic ablation region 122 that contracts or is reduced in size (represented by "−") while the non-ablation region 431 is enlarged (represented by "+") and the other non-ablation region 432 at the distal end 413 remains unchanged.

Figure 10:
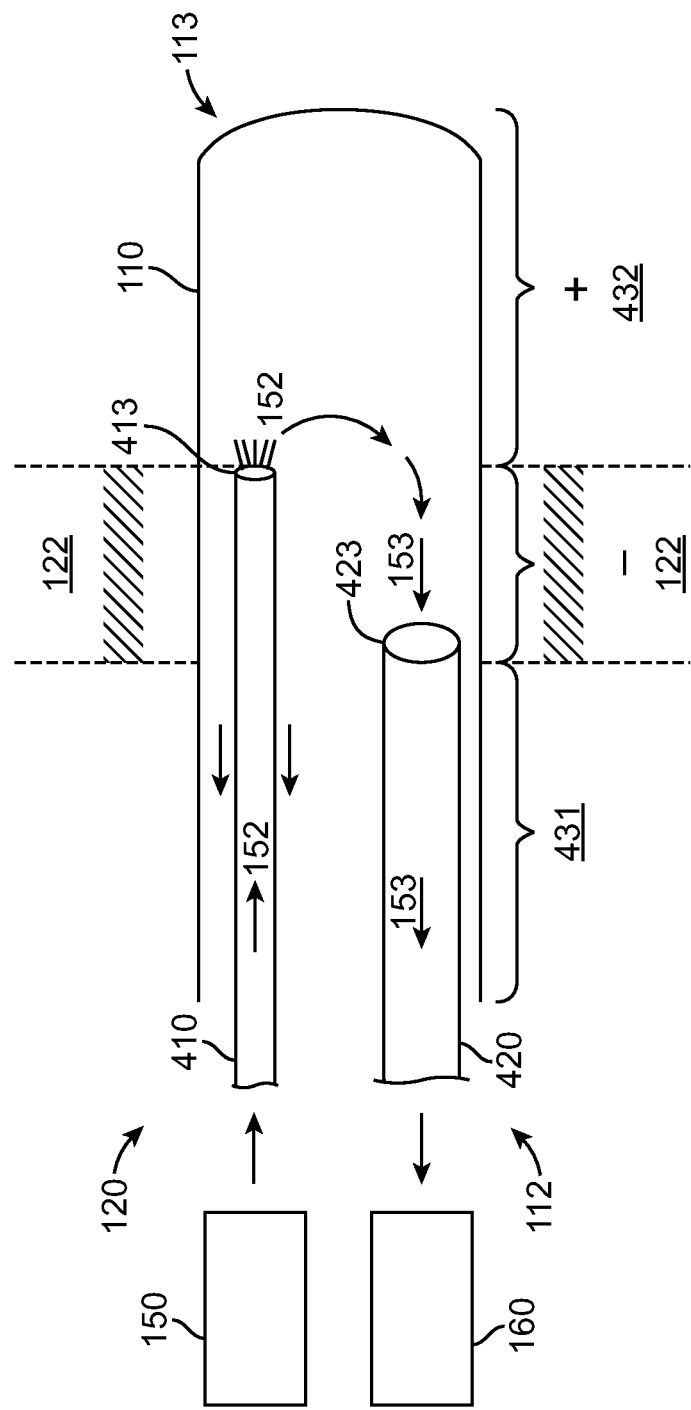
FIG. 10 illustrates the movable cooling assembly shown in FIG. 4 in which a coolant tube is moved towards a proximal end of the ablation device to reduce a cryogenic ablation region.

Referring to FIG. 10, according to another embodiment, the first tube 410 that carries coolant 152 is moved or pulled back towards the proximal end 112 of the ablation device 110 while the second inner tube 420 remains in the same position, thereby reducing or focusing the cryogenic ablation region 122 (represented by "−") while the distal non-ablation region 432 is enlarged (represented by "+") and the other, proximal non-ablation region 431 remains the same.

While FIGS. 9 and 10 illustrate movement of a single tube to reduce or focus the cryogenic ablation region 122, but in another embodiment, the first tube 410 may be pulled back towards the proximal end 112 of the ablation device 110, and the second tube 420 may be pushed forward towards the distal end 113 of the ablation device, separately or simultaneously, thereby reducing or focusing the cryogenic ablation region 122.

Figure 11:
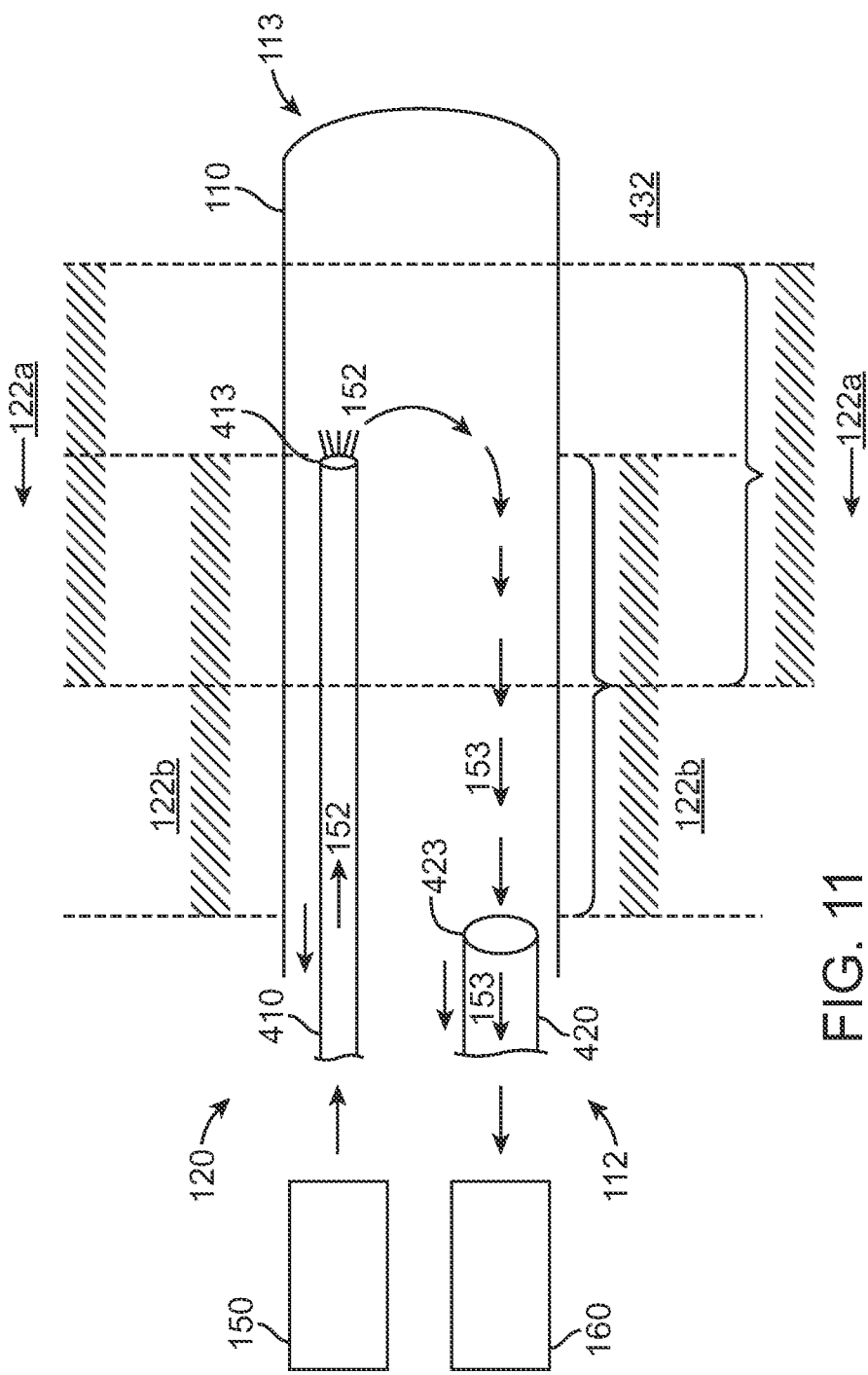
FIG. 11 illustrates the movable cooling assembly shown in FIG. 4 in which a coolant tube and an exhaust tube are moved to reposition a cryogenic ablation region.

Referring to FIG. 11, according to another embodiment, both of the first and second tubes 410, 420 may be moved, separately or together, in the same direction to re-position a cryogenic ablation region 122. In the illustrated embodiment, the first and second tubes 410, 420 are pulled back towards the proximal end 112 of the ablation device 110 such that the cryogenic ablation region 122a, which may or may not remain the same size during this process, is re-positioned to be at location 122b closer to the proximal end 112 of the ablation device 110. A similar re-positioning adjustment may be made by pushing the first and second tubes 410, 420 towards the distal end 413 of the ablation device 110.

Embodiments of a movable cooling assembly 120 may be utilized with various types of cryogenic ablation devices 110 (as generally illustrated in FIGS. 1 and 3). FIGS. 12-21 illustrate different embodiments of cryogenic balloon devices or catheters 305 and how a movable cooling assembly 120 may be utilized with these balloon ablation devices 305 to adjust ablation regions 122.

Figure 12:
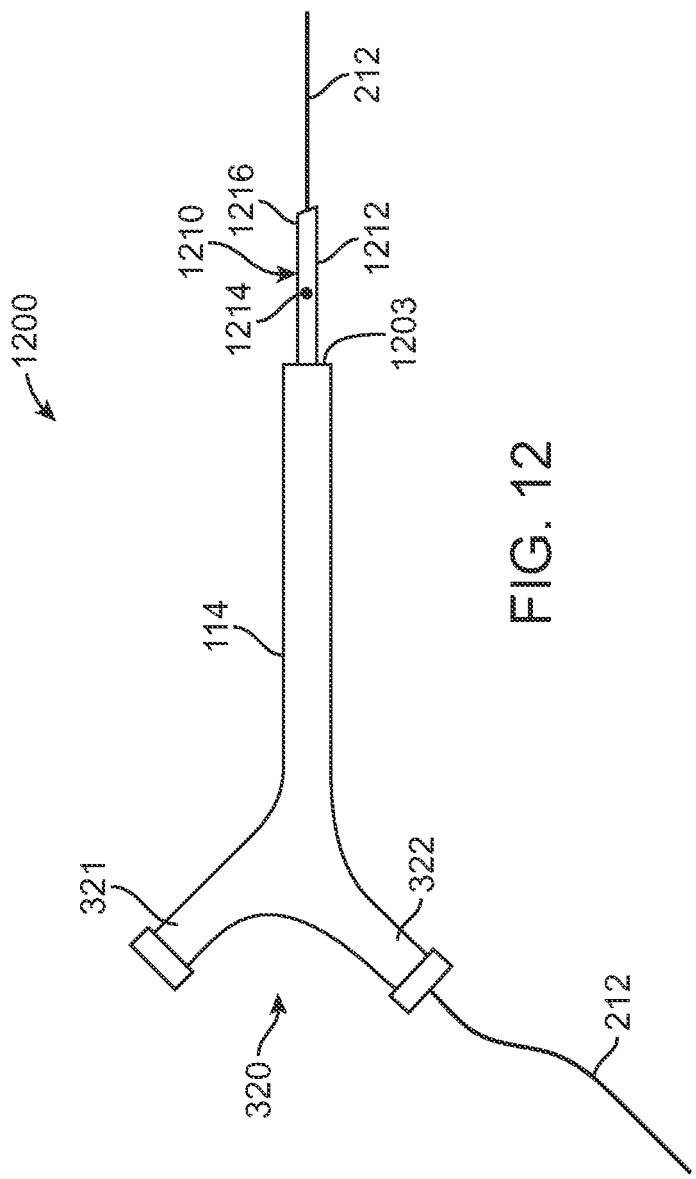
FIG. 12 generally illustrates a cryogenic ablation instrument including a balloon according to one embodiment.

Referring to FIG. 12, a cryogenic ablation device 1200 constructed according to one embodiment is in the form of a cryogenic balloon catheter that includes an elongate, flexible body, support member or shaft 114 (generally referred to as a support member 114 in these embodiments). The support member 114 is similar to the body 114 described above except that in the illustrated embodiment, the distal end 1203 of the support member 114 is open such that a cryogenic balloon 1210 extends from the support member 114. The balloon 1210 may include a body 1212, which may support or carry mapping electrodes 1214 or other similar sensors. A guide wire 212 may extend through the body 1212 to facilitate positioning and manipulation of the balloon 1210 within a patient.

Figure 13:
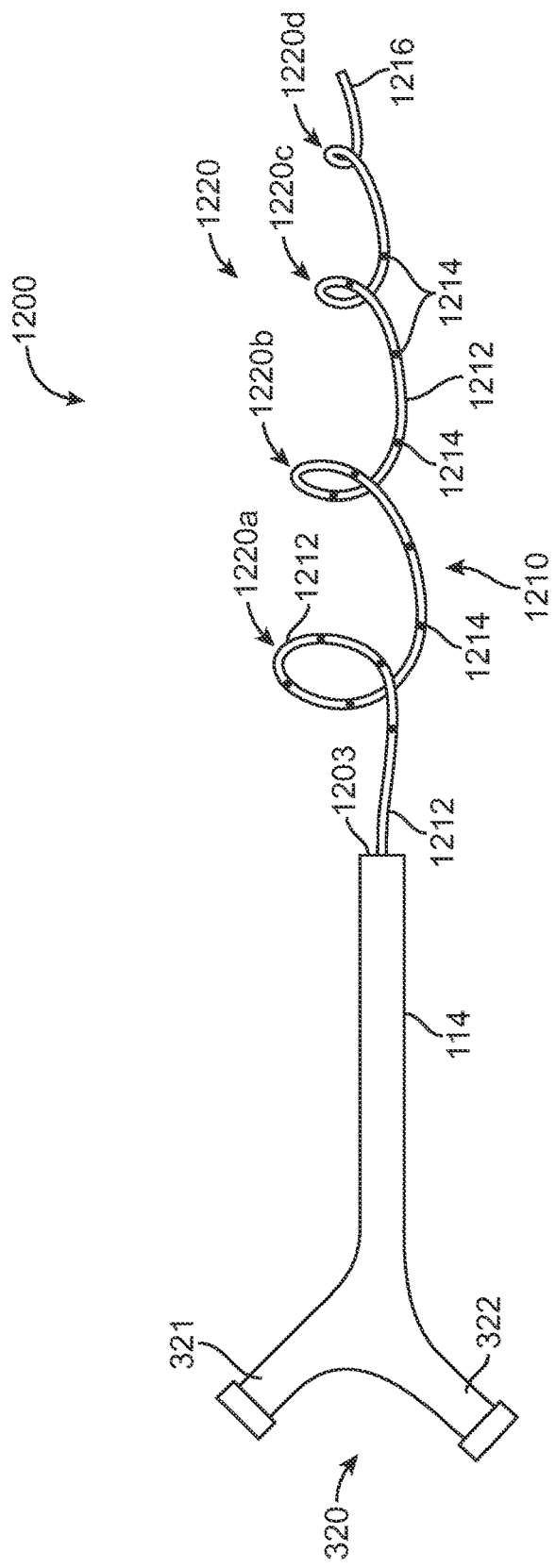
FIG. 13 further illustrates the balloon deployed from a support member and assuming a spiral or helical shape.

Referring to FIG. 13, when deployed from the support member 114, the balloon 1210 may assume a spiral, wound, corkscrew or helical shape 1220 (generally referred to as helical shape 1220), which may be particularly suitable for insertion into an antrum of a pulmonary vein (PV) or other converging cavities or lumens as shown in FIGS. 14 and 15. Suitable balloons 1210 that may be used for this purpose may be made of Pebax and have an inflated outer diameter of about 5 millimeters and a wall thickness of about 0.001". With this configuration, a cryogenic ablation region 122 may be defined between a first pre-defined location along the helical body 1212 and a second pre-defined location of the helical body 1212 to chill or ablate an arc-like or circular region around an inner surface of an entrance or antrum of a pulmonary vein.

In the embodiment shown in FIGS. 13-15, the helical balloon body 1210 assumes or is formed into a plurality of turns or loops. For this purpose, the balloon body 1210 may be made of a memory alloy or include a wire or ribbon made of a memory alloy such that the balloon body 1210 assumes a helical shape 1220 when deployed. According to one embodiment, the deployed balloon body 1210 assumes a helical shape 1220 having four turns or loops 1220a-d, which define a continuously decreasing outer diameter along a length of the helical body 1210 and towards the distal end 1216 of the helical body 1210. According to one embodiment, the first or largest turn or loop 1220a may define an outer diameter of about 32 mm, the second turn or loop 1220b may define an outer diameter of about 28 mm, the third turn or loop 1220c may define an outer diameter of about 24 mm, and the fourth or smallest turn or loop 1220d may define an outer diameter of about 20 mm. Such configurations are particularly suitable for positioning within an antrum of a pulmonary vein since the decreasing diameter loops 1220 generally correspond to the shape of the antrum of a pulmonary vein. Other dimensions and numbers of loops may be utilized as appropriate.

The helical balloon 1210 may provide a circular spiral footprint having a width of about 4-5 mm, which is well suited for cryo-ablation of, for example, cardiac tissue and, in particular, tissue of pulmonary veins. This narrow footprint also facilitates a sharply defined cryogenic ablation pattern of a predictable depth while utilizing less coolant 152 than known balloon devices. Moreover, the material of the helical balloon 1210 may be compliant or semi-compliant such that the helical balloon 1210 is not very stiff along the axis of the helical-shaped sections 1220. As a result, when the helical balloon 1210 is pressed against a tissue surface having a "funnel-like" shape, the helical coils 1220a-d collapse or compress or form a funnel-like shape. Further, the cross-sectional diameter of the balloon 1210 is sufficiently small such that tensile stresses on the wall of the balloon 1210 resulting from the balloon 1210 being filled with coolant 152 are reduced. Lower stress levels on the balloon 1210 reduce the risk that the balloon 1210 will burst.

It is estimated that spiral or helical balloon 1210 including a proximal turn section having an outer diameter of about 32 mm and tighter turn radii of about 28 mm, 24 mm and 20 mm is suitable for insertion within an antrum of a pulmonary vein, and a chillable length of a balloon 1210 may have a length of about 350 mm, or about 1 foot, based on the length estimation of $\pi*(32 \text{ mm}+28 \text{ mm}+24 \text{ mm}+20 \text{ mm})$. With a 350 mm long chillable balloon 1210 length, the length that may form a single-turn cryogenic ablation region 122 having a length of about 90 mm. Thus, if the tissue contact area is about 360 mm$^2$ (estimated by 4 turns*90 mm), an amount of power can be estimated, e.g., assuming negligible cooling effect losses due to blood flow and utilizing Ozen Engineering's heat flow simulation. This simulation results in a value of about $20\times10^3$ Watts/m$^2$ during a duration of about 40 seconds, which is about $20\times10^{-2}$ Watts/mm$^2$. Given a contact area of about 360 mm$^2$, the estimated amount of power required for 90 seconds of cryogenic ablation to achieve tissue temperatures less than $-40°$ C. at a tissue depth of about 4 mm would be about 72 Watts, which results in about 6,480 Joules cooling, estimated by 90 seconds*72 Watts. Based on an assumption that the cooling capacity of nitrous oxide at $-70°$ C. is about 150 J/gram, an estimated total of about 43 grams of nitrous oxide is required to achieve desired cryogenic ablation, thus indicating that embodiments may be successfully implemented.

Embodiments of a cooling assembly 120 may be utilized with the helical or spiral balloon 1210 described with reference to FIGS. 12-15. In one embodiment, referring to FIG. 16, method 1600 of cryogenically ablating tissue using the balloon 1210 shown in FIGS. 12-15 and the movable cooling assembly 120 described with reference to FIGS. 1-11 includes, at stage 1605, deploying the helical cryogenic balloon 1210 from a support member, catheter shaft, or other suitable body 114, as shown in FIG. 13, and positioning the balloon 1210 adjacent to target tissue to be ablated. For example, as shown in FIGS. 14 and 15, the helical balloon 1210 may be inserted within an antum of a pulmonary vein. If necessary, mapping electrodes 1214 may be utilized to emit and detect non-ablative energy to assess the location of tissue to be ablated. Mapping procedures can be performed before and after cryo ablation.

With further reference to FIG. 16, at stage 1610, a first tube 410 that carries coolant 152 may be positioned within a lumen 1218 of the balloon 1210, and at stage 1615, a second or exhaust tube 420 may be positioned within the lumen 1218. As discussed above with reference to FIGS. 4-11, a cryogenic ablation region 122 is defined between the distal ends 413, 423 of the first and second tubes 410, 420. In the illustrated embodiment, the cryogenic ablation region 122 has a certain curvature corresponding to the helical-shaped lumen 1218 of the balloon 1210. At stage 1620, a refrigerant or coolant 152, such as nitrous oxide, is delivered through the first tube 410 to ablate tissue within or adjacent to the cryogenic ablation region 122, and at stage 1625, used or spent refrigerant 153 is exhausted through the second tube 420. At stage 1630, at least one tube may be moved, e.g., slidably moved, within the helical-shaped lumen 1218 to adjust the cryogenic ablation region 122. As discussed above with respect to FIGS. 4-11, the cryogenic ablation region 122 may be enlarged, reduced and/or re-positioned by moving only the first tube 410, only the second tube 420, or both of the first and second tubes 410, 420, and the cryogenic ablation region 122 may be re-positioned by moving both of the first and second tubes 410, 420.

After any required adjustment of the cryogenic ablation region 122, further cryogenic ablation may be performed and/or mapping electrodes 1214 may be utilized to emit and detect non-ablative energy to assess whether further ablation is required. Thus, with embodiments, the same device may be used to perform therapeutic or ablative procedures as well as diagnostic procedures (e.g., determining locations of ablation regions and determining effectiveness of ablation) without removing the device or exchanging the device with another device having different functionality.

Referring to FIG. 18, a cryogenic ablation device 1800 constructed according to another embodiment includes a plurality of inflatable elements or balloons. In the illustrated embodiment, the cryogenic ablation device 1800 includes a first balloon 1810, which may be a cryogenic balloon that extends from a support member or catheter shaft (generally identified as 114, e.g., similar to the support member 114 described with reference to FIG. 12) and a second, cryogenic balloon 1820 that extends from the support member 114. The second balloon 1820 may be attached or adhered to the first balloon 1810.

In one embodiment, the first balloon 1810 is an inner or central balloon made of Pebax® or other suitable materials, and when inflated, may have a variable outer diameter ranging from about 0.25" to about 1.5". The thickness of the balloon 1810 wall may be about 1/16" to about 1/32". According to one embodiment, the second balloon 1820 is similar to or the same as the helical balloon 1210 described with reference FIGS. 12-17, and may be made of the same or similar materials and have similar dimensions.

Thus, the first balloon 1810 has a first shape, and the second balloon 1820 has a second shape different than the first shape. In the illustrated embodiment, the first balloon 1810 extends from the support member 114 and has a generally bulbous, spherical, or spheroid shape 1812 or other suitable shape that may correspond to an anatomical structure when inflated, and the second balloon 1820, e.g., balloon 1210, may have a helical or helical or spiral like shape such that the second or coolant delivery balloon 1820 wraps or spirals around at least a portion of the outer surface of the first or central balloon 1810. Thus, in the illustrated embodiment, the cryogenic ablation device 1800 includes balloons 1810, 1820 having different cross-sectional shapes, and one balloon, the second or helical balloon 1810 in the illustrated embodiment, has a cross-sectional shape that is substantially constant along its length whereas the first or central balloon 1810 has cross-sectional area that substantially varies along its length.

According to one embodiment, the first or central balloon 1810 may extend through a space defined by the loop or circle defined by the second portion 1832 of the second balloon 1820. In one embodiment, the first balloon 1810 has a spheroid or bulbous shape and may be particularly suitable for blocking blood flow from a pulmonary vein, thereby serving as a thermal insulator and to reduce cooling losses to flowing blood, thereby facilitating more effective cryo-ablation. Additionally, the first or central balloon 1810 may be filled with a thermal insulator, e.g. foam, to prevent heat transfer to the pulmonary vein. This configuration reduces the amount of coolant 152 needed and also may reduce the potential for damage to adjacent structures.

In the illustrated embodiment, a first portion 1831 of the second balloon 1820 extends laterally across a length of the outer surface of the first balloon 1810 with a slight curvature or helical or spiral like shape, leading to a second portion 1832, which extends or wraps around a circumferential section of the outer surface of the first balloon 1810. In the illustrated embodiment, the first portion 1831 of the second balloon 1820 wraps partially around the first balloon 1810 as it extends along the outer surface of the first balloon 1810. In other embodiments, the first portion 1831 may have a more pronounced helical or spiral shape having additional turns or loops such that the second balloon 1820 may wrap helically or spirally around additional portions of the first or central balloon 1810. The manner in which refrigerant is supplied to and exhausted is similar to the manner illustrated in, e.g., FIG. 4 and other Figures, which illustrate use of supply and exhaust tubes 410, 420.

Referring to FIG. 19, embodiments of multi-balloon ablation devices, e.g., as shown in FIG. 18, may be utilized in methods 1900 to create transmural blocking lesions within a PV antrum, e.g., to treat atrial fibrillation. In the illustrated embodiment, the method 1900 includes, at stage 1905, positioning the multi-balloon ablation device 1900 adjacent to target tissue to be ablated. One or both of the balloons 1810, 1820 may carry mapping electrodes which may, for example, be used to determine the appropriate positioning of the device 1800 prior to ablation. In one embodiment, the second balloon 1820 is in the form of a helical or helical-like balloon 1210 and includes (mapping electrodes 1214.

At stage 1910, the first or central balloon 1810 is inflated, e.g., with $N_2O$ (nitrous oxide) gas or another suitable gas, such as $O_2$ (oxygen) gas, which is in fluid communication with the inner space or lumen of the first balloon 1810. For this purpose, and as generally illustrated in FIG. 4, for example, the interior of the first or central balloon 1810 may be in fluid communication with the elongate body or support member 114 (as shown in FIG. 18) and a source of gaseous nitrous oxide to facilitate inflation of the first balloon 1810. The support member 114 may also include an exhaust lumen for exhausting spent gaseous nitrous oxide or other gas from the first balloon 1810 in order to maintain the desired pressure within the first balloon 1810. When the first balloon 1810 is inflated, the first balloon 1810 presses the second balloon 1820, e.g., complete or partial helical coils, loops or turns, against the inside wall of the atrium, facilitating diagnostic functions such as mapping of electrical activity inside the atrium and facilitating effective cryogenic ablation.

At stage 1915, coolant 152 for cryogenically ablating tissue is delivered through the second or helical balloon 1820, thereby ablating adjacent to portions of the second balloon 1820 through which coolant 152 flows or is dispersed. In embodiments in which the second or helical balloon 1820 includes mapping electrodes 1214, the mapping electrodes 1214 may be used to assess the effect of ablation utilizing non-therapeutic energy emitted and detected by the mapping electrodes 1214.

Referring to FIGS. 20 and 21, movable cooling assembly or ablation adjustment element 120 embodiments may be incorporated into embodiments of multi-balloon cryogenic devices, e.g., the multi-balloon device 1800 including two balloons 1810, 1820 as shown in FIG. 18. According to one embodiment, the movable cooling assembly 120 is positioned within the second or helical shaped balloon 1820, and the inner or first or inner balloon 1810 is inflated to press the spiral sections of the second balloon 1820 against tissue to be ablated. The cooling assembly 120 within the second balloon 1820 can be manipulated to adjust the cryogenic ablation region 122.

More particularly, referring to FIG. 21, a method 2100 of cryogenically ablating tissue includes, at stage 2105, positioning a multi-balloon apparatus 1800 adjacent to target tissue to be ablated, e.g., within an antrum of a pulmonary vein, as shown in FIG. 20. At stage 2110, the first tube 410 of the cooling assembly 120 that carries a refrigerant 152 is positioned within the lumen 1218 of the second or outer balloon 1820, and at stage 2115, the second tube 420 of the cooling assembly 120 that exhausts coolant 153 is positioned within the lumen 1218 of the second or helical balloon 1820. In the illustrated embodiment, the first tube 410 extends farther into the second balloon 1820 than the second tube 420, thereby defining a cryogenic ablation region 122 between the distal ends 413, 423 of the first and second tubes 410, 420. In another embodiment, the second tube 420 may extend farther beyond the first tube 410, but FIG. 20 illustrates an embodiment in which the first tube 410 extends beyond the second tube 420. FIG. 20 also illustrates the distal ends 413, 423 extending through the first portion 1831 of the second balloon 1820, but during use, the distal ends 413, 423 of the tubes 410, 420 of the movable cooling assembly 120 may be positioned within different sections of the second balloon 1820, e.g., within the second portion 1832 to define a desired cryogenic ablation region 122 at a desired location.

At stage 2120, the first or inner balloon 1810 is inflated, thereby pressing the second or outer balloon 1820 and the first and second tubes 410, 420 therein against tissue to be ablated. At stage 2125, coolant 152 is delivered through the second balloon 1820, i.e., through the first inner tube 410 of the cooling assembly 120, and dispensed into the lumen 1218 of the second balloon 1820 through the nozzle 440. As a result, at stage 2130, tissue adjacent to the cryogenic ablation region 122 defined between the distal ends 413, 423 of the first and second tubes 410, 420 within the second balloon 1829 is cryogenically ablated, and spent coolant 153 is exhausted from the second balloon 1820 through the second inner tube 420.

During the procedure, at stage 2135, a clinician may adjust the location of ablation by moving one or both of the first and second inner tubes 410, 420. For example, as discussed above with reference to FIGS. 4-11, the cryogenic ablation region 122 may be expanded or reduced by moving only the first tube 410, only the second tube 420, or both of the first and second tubes 410, 420, and a cryogenic ablation region 122 may be re-positioned by moving both of the first and second tubes 410, 420. After any required adjustment of the cryogenic ablation region 122, further cryogenic ablation may be performed and/or mapping electrodes may be utilized to assess whether tissue should be ablated or to determine the effectiveness of ablation.

Although particular embodiments have been shown and described, it should be understood that the above discussion is not intended to limit the scope of these embodiments. Various changes and modifications may be made without departing from the scope of the claims.

For example, embodiments may be configured to perform ablation of various types of tissue for treatment of different conditions or diseases, one example of which is to perform endocardial ablation to treat atrial fibrillation as described above. Moreover, although embodiments are described with reference to ablation utilizing nitrous oxide, different types of coolants and refrigerants may also be utilized.

Further, although certain multi-balloon embodiments are described with reference to two balloons, embodiments may also be implemented using more than two balloons. For example, in another embodiment, a cryogenic device may include an inner balloon and two or more outer balloons that at least partially wrap around the outer balloon. Nitrous oxide may then be supplied through multiple outer balloons. Further, a movable cooling assembly may be incorporated into multiple outer balloons or each outer balloon to adjust respective cryogenic ablation regions as desired. Moreover, although embodiments of spiral or helical balloons are described with reference to spiral or helical balloons having approximately four turns or coils, embodiments may include other numbers of turns and spirals, e.g., depending on the cavity or lumen into which the ablation device is to be inserted. Further, although multi-balloon device embodiments are described with respect to balloon elements that are attached or adhered together, the balloon components may also be attached together using rapid exchange components.

Thus, embodiments are intended to cover alternatives, modifications, and equivalents that may fall within the scope of the claims.

What is claimed is:

1. A cryogenic ablation apparatus, comprising:
an elongate flexible shaft;
a flexible body extending from the elongate flexible shaft, the flexible body defining a lumen; and
a movable cooling assembly including:
a first tube that is axially movable relative to the flexible body and has a first distal end that is unattached to the flexible body, the first tube being positioned within the lumen of the flexible body and including a first opening positioned to supply a refrigerant into the lumen of the flexible body; and
a second tube that is axially movable relative to the flexible body and has a second distal end that is unattached to the flexible body, the second tube being positioned within the lumen of the flexible body and include a second opening positioned to exhaust spent refrigerant from the lumen of the flexible body.

2. The cryogenic ablation apparatus of claim 1, wherein the first and second tubes are movable together.

3. The cryogenic ablation apparatus of claim 1, wherein the first and second tubes are movable independently.

4. The cryogenic ablation apparatus of claim 1, further comprising at least a first temperature sensor disposed within a distal region of the flexible body.

5. The cryogenic ablation apparatus of claim 1, wherein the first and second tubes are disposed coaxially.

6. The cryogenic ablation apparatus of claim 1, wherein the first and second tubes are parallel to and spaced apart from each other.

7. The cryogenic ablation apparatus of claim 1, wherein the first and second tubes are different diameters.

8. The cryogenic ablation apparatus of claim 7, wherein the first tube has a diameter smaller than a diameter of the second tube.

9. The cryogenic ablation apparatus of claim 1, wherein the first tube has a plurality of apertures in a distal region thereof.

10. A method of cryogenically ablating tissue, comprising:
positioning a cryogenic ablation apparatus adjacent to tissue to be ablated, the cryogenic ablation apparatus comprising an expandable body extending from an elongate flexible shaft and a movable cooling assembly including a first tube that is axially movable relative to the expandable body and has a first distal end that is unattached to the expandable body, the first tube being positioned within a lumen of the expandable body and having an opening positioned to supply a refrigerant into the lumen of the expandable body, the movable cooling assembly further including a second tube that is axially movable relative to the expandable body and has a second distal end that is unattached to the expandable body, the second tube being positioned within a lumen of the expandable body and having a second opening positioned to exhaust spent refrigerant from the lumen of the expandable body;
expanding the expandable body, thereby pressing the body against tissue to be ablated;
axially moving one or both of the first tube and the second tube relative to the body lumen to place one or both of the first distal end of the first tube and the second distal end at a desired location;
delivering a refrigerant through the first tube into the lumen of the expandable body to thereby cryogenically ablate tissue contacted by the expandable body; and
evacuating spent coolant from the lumen of the expandable body through the second tube.

11. The method of claim 10, wherein adjusting at least one of a size and location of a cryogenic tissue ablation region includes axially moving the first and second tubes together.

12. The method of claim 10, wherein adjusting at least one of a size and location of a cryogenic tissue ablation region includes axially moving the first and second tubes independently.

13. The method of claim 10, wherein adjusting at least one of a size and location of a cryogenic tissue ablation region includes moving the second tube proximally relative to the first tube.

14. The method of claim 10, wherein adjusting at least one of a size and location of a cryogenic tissue ablation region includes moving the first tube distally relative to the second tube.

15. The method of claim 10, wherein adjusting at least one of a size and location of a cryogenic tissue ablation region includes moving the second tube distally relative to the first tube.

16. The method of claim 10, wherein adjusting at least one of a size and location of a cryogenic tissue ablation region includes moving the first tube proximally relative to the second tube.

17. The method of claim 10, wherein adjusting at least one of a size and location of a cryogenic tissue ablation region includes moving both the first and second tubes proximally or distally relative to the expandable body.

18. A cryogenic ablation apparatus, comprising:
an elongate flexible shaft;
a flexible body extending from the elongate flexible shaft, the flexible body defining a lumen;
one or more mapping electrodes disposed on the flexible body; and
a movable cooling assembly including a first tube being unattached to and axially movable relative to the flexible body and having an open first distal end positioned within and opening into the lumen of the flexible body to supply a refrigerant to the body lumen, and a second tube being unattached to and axially movable relative to the flexible body and having an open second distal end positioned within and opening into the lumen of the flexible body to exhaust spent refrigerant from the body lumen.

* * * * *